(12) United States Patent
Atlee et al.

(10) Patent No.: US 9,220,450 B2
(45) Date of Patent: Dec. 29, 2015

(54) COMPOSITIONS AND METHODS FOR MEASUREMENT OF OXYGEN SATURATION IN BLOOD FILLED STRUCTURES

(71) Applicant: ESO-TECHNOLOGIES, INC., Middleton, WI (US)

(72) Inventors: John L. Atlee, Hartland, WI (US);
Stephen H. Gorski, Eagle, WI (US);
Bonnie J. Reinke, Middleton, WI (US);
Christian G. Reikersdorfer, Middleton, WI (US); Eugene Palatnik, Pewaukee, WI (US); Elena Bezrukova, Middleton, WI (US); Michael M. Bohachek, Belgium, WI (US)

(73) Assignee: ESO-TECHNOLOGIES, INC., Middleton, WI (US)

( * ) Notice: Subject to any disclaimer, the term of this patent is extended or adjusted under 35 U.S.C. 154(b) by 0 days.

(21) Appl. No.: 14/117,474

(22) PCT Filed: Jun. 18, 2013

(86) PCT No.: PCT/US2013/046385
§ 371 (c)(1),
(2) Date: Nov. 13, 2013

(87) PCT Pub. No.: WO2014/011368
PCT Pub. Date: Jan. 16, 2014

(65) Prior Publication Data
US 2015/0112172 A1    Apr. 23, 2015

Related U.S. Application Data

(60) Provisional application No. 61/661,047, filed on Jun. 18, 2012.

(51) Int. Cl.
| | | |
|---|---|---|
| *A61B 5/1455* | (2006.01) |
| *A61B 5/1459* | (2006.01) |
| *A61B 5/0205* | (2006.01) |
| *A61B 5/042* | (2006.01) |
| *A61B 5/00* | (2006.01) |
| *A61B 7/02* | (2006.01) |
| *A61B 5/01* | (2006.01) |

(52) U.S. Cl.
CPC .......... *A61B 5/1459* (2013.01); *A61B 5/02055* (2013.01); *A61B 5/0421* (2013.01); *A61B 5/0422* (2013.01); *A61B 5/14552* (2013.01); *A61B 5/6853* (2013.01); *A61B 5/72* (2013.01); *A61B 5/742* (2013.01); *A61B 7/023* (2013.01); *A61B 5/01* (2013.01); *A61B 2562/0233* (2013.01); *A61B 2562/0247* (2013.01)

(58) Field of Classification Search
CPC ............... A61B 5/1459; A61B 5/1455; A61B 5/14551; A61B 5/14552; A61B 5/6852; A61B 5/6853; A61B 5/72
See application file for complete search history.

(56) References Cited

U.S. PATENT DOCUMENTS 5,005,573 A * 4/1991 Buchanan ............ A61B 5/1459
600/338
5,370,679 A 12/1994 Atlee, III
(Continued)

*Primary Examiner* — Eric Winakur
(74) *Attorney, Agent, or Firm* — Kirk J. Hogan; Casimir Jones, S.C.

(57) ABSTRACT

Provided herein is technology relating to medical monitoring of physiologic parameters, and particularly, but not exclusively, relating to compositions, methods and systems for the measurement of venous and arterial oxygen saturation in the blood of blood-filled anatomical structures.

30 Claims, 25 Drawing Sheets

(56) References Cited

U.S. PATENT DOCUMENTS

| | | |
|---|---|---|
| 5,394,880 A | 3/1995 | Atlee, III |
| 5,570,671 A | 11/1996 | Hickey |
| 5,715,816 A | 2/1998 | Mainiero et al. |
| 5,785,051 A * | 7/1998 | Lipscher ................. A61B 5/06 128/200.26 |
| 6,626,841 B1 | 9/2003 | Atlee, III |
| 6,760,609 B2 | 7/2004 | Jacques |
| 2009/0318787 A1 | 12/2009 | Aoyagi et al. |
| 2010/0198027 A1 | 8/2010 | Dixon |
| 2012/0116156 A1 * | 5/2012 | Lederman ................. A61B 1/05 600/109 |
| 2012/0123286 A1 * | 5/2012 | Wilson ................. A61B 5/6852 600/529 |
| 2012/0215074 A1 * | 8/2012 | Krimsky ............ A61B 5/02158 600/300 |

* cited by examiner

COMPOSITIONS AND METHODS FOR MEASUREMENT OF OXYGEN SATURATION IN BLOOD FILLED STRUCTURES

CROSS-REFERENCE TO RELATED APPLICATIONS

The present Application claims priority to U.S. Provisional Application Ser. No. 61/661,047 filed 18 Jun. 2012, the entirety of which is incorporated by reference herein.

FIELD OF THE TECHNOLOGY

Provided herein is technology relating to medical monitoring of physiologic parameters, and particularly, but not exclusively, relating to compositions, methods and systems for the measurement of venous and arterial oxygen saturation in the blood of blood-filled anatomical structures.

BACKGROUND

The ability to monitor the balance between oxygen supply and demand, and to assess the impact of medical and surgical interventions on this balance, is of vital importance to the patient and the caregiver. Non-invasive methods (e.g., physical exam, pulse oximetry), and invasive methods (e.g., blood gas analysis, oximetric catheters) are currently employed to assess venous and/or arterial oxygen saturation. For example the pulmonary artery catheter (PAC) requires insertion via a central (e.g., jugular or subclavian) vein, and advancement through the patient's heart chambers to place the catheter tip into the pulmonary artery. Although the PAC provides valuable information regarding the patient's oxygen and cardiac status, it's placement and maintenance is invasive, requires special training to insert, and is fraught with risks, safety issues and adverse events including vascular perforation, infection, occlusion and bleeding. The central venous pressure catheter (CVP) is also placed in a large vein in the neck, chest, or groin and directed to a major venous structure near the heart. Both PAC and CVP catheters require anticoagulant and saline flushing to keep fluid lines open.

Accordingly, minimally invasive methods and systems for the measurement of venous and arterial oxygen saturation in the blood of blood-filled anatomical structures are needed.

SUMMARY

Provided herein is technology that facilitates measuring and monitoring of venous oxygen saturation, both mixed and central, as well as arterial oxygen saturation, via minimally invasive compositions, methods and systems for measurement of blood oxygen saturation in blood-filled anatomic structures. In one embodiment, the technology provides an esophageal sensor of vital information with reduced costs, risks and training compared, for example, to the PAC and CVP. Because of its proximity to the heart and vessels in the chest of human beings, the esophagus has been used for ultrasonic visualization of cardiac structures via transesophageal echocardiography (TEE), stethoscopic auscultation of respiratory and cardiac sounds, and core temperature. In some embodiments, advantage is taken of anatomical sites for the measurement of oxygen saturation (i.e., mixed venous, central venous, systemic arterial oxygen saturation) using an oxygen saturation sensor placed in the esophagus in combination with technologies that enable effective deployment and discrimination of the signals. In other embodiments, the measurement and monitoring compositions, methods and systems described herein are applicable to quantification of oxygen saturation in other vessels and blood filled structures. In further embodiments, the measurement and monitoring compositions, methods and systems described herein may also be used in surface oximetry.

Additional embodiments will be apparent to persons skilled in the relevant art based on the teachings contained herein.

BRIEF DESCRIPTION OF THE DRAWINGS

These and other features, aspects, and advantages of the present technology will become better understood with regard to the following drawings.

It is to be understood that the figures are not necessarily drawn to scale, nor are the objects in the figures necessarily drawn to scale in relationship to one another. The figures are depictions that are intended to bring clarity and understanding to various embodiments of apparatuses, systems, and methods disclosed herein. Moreover, it should be appreciated that the drawings are not intended to limit the scope of the present teachings in any way.

DETAILED DESCRIPTION

Provided herein is technology relating to medical monitoring of physiologic parameters, and particularly, but not exclusively, relating to compositions, methods and systems for the measurement of venous and arterial oxygen saturation in the blood of blood-filled anatomical structures. In some embodiments, an opto-electronic sensor or multiplicity of sensors on an esophageal probe is provided for use with signal processing methods wherein the probe is deployed to measure, monitor and report oxygen saturation (e.g., central venous, mixed venous, and arterial oxygen saturation) from blood filled cardiac chambers and vessels in the chest in proximity to the esophagus and other anatomical sites. In preferred embodiments, methods are provided to optimally deploy and position the sensor or sensors in relation to anatomic structures of interest.

Esophageal Probe

Figure 1:
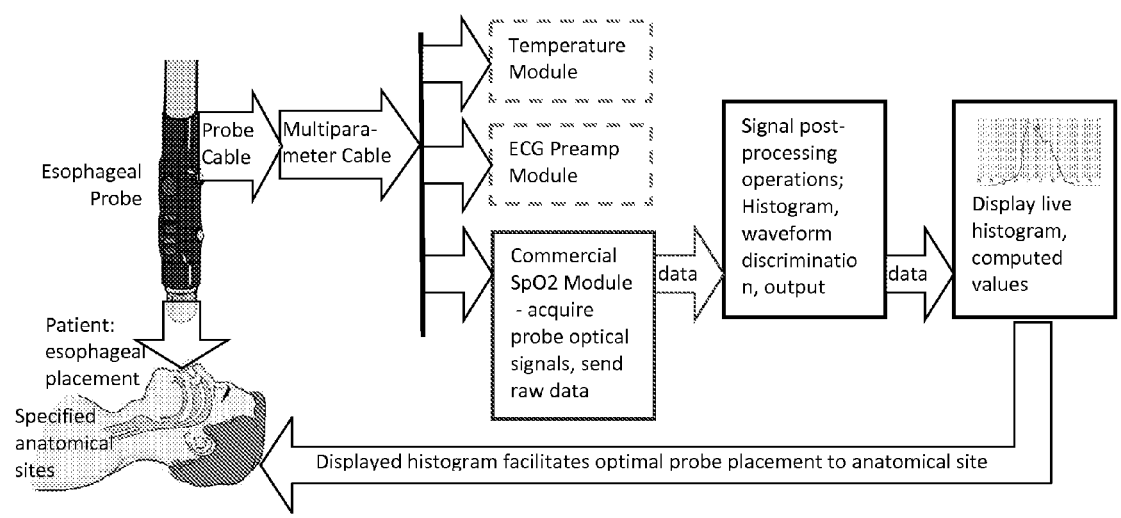
FIG. 1 illustrates the system architecture of an embodiment of the technology described herein.

As shown in FIG. 1, in one embodiment, an esophageal probe is placed into a patient using methods described herein. In some embodiments, the esophageal probe comprises a cable which connected to a physiological parameter monitor that monitors temperature, electrocardiogram (ECG), and pulse oximetry by means of a multi-parameter cable. In further embodiments, temperature and ECG measurements are suitably obtained from the probe by various means known in the art. A pulse oximeter module is used to continuously generate and measure signals in sensor elements in the probe. Pulse oximeter modules that are commercially available include the ChipO2 pulse oximeter module, model Protocol 'A' from ITEC Engineering (Pewaukee, Wis., USA), and the ChipOx miniaturized pulse oximeter module, model CS10100, from Corscience (Erlangen, Bavaria, Germany) and are examples of modules which are suitably employed. The raw data output stream of the pulse oximeter module provides an input stream for signal processing operations. With the probe positioned in proximity to target anatomical sites, the signal processing method provides a real time graphical output as a histogram or other suitable representation, used by an operator to deploy and optimize the probe placement to a specified anatomical site.

Figure 2:
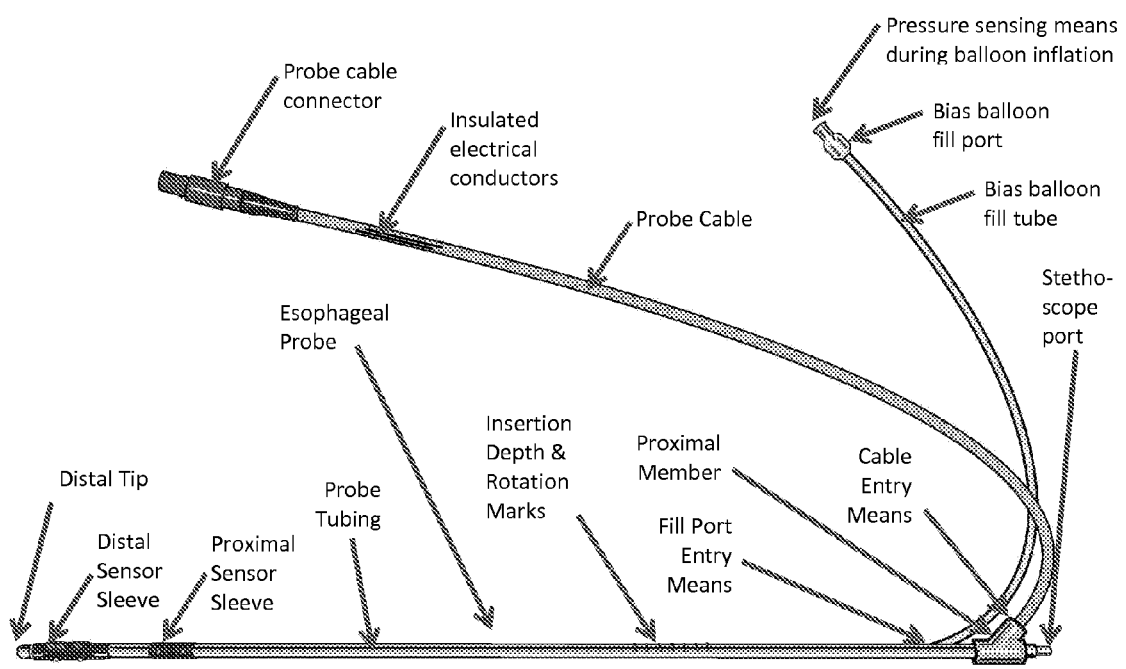
FIG. 2 illustrates an embodiment of an esophageal probe described herein.

As shown in FIG. 2, an esophageal probe comprises as a length of flexible biocompatible tubing upon which is mounted at least one sensor containing sleeve, for example, a distal sleeve and proximal sleeve both containing sensor elements. The distal tip of the probe is rounded to facilitate safe insertion into the patient. In certain embodiments, the proximal portion of the probe comprises a proximal member which comprises a stethoscope port which accepts a stethoscope earpiece, a means of cable entry for the probe cable, and a means of entry for at least one balloon fill tube with a fitting such as Luer-type fitting. In further embodiments, the probe cable contains a suitable number of insulated electrical conductors for the sensors, and a medical-grade connector. In some embodiments, the probe's length is marked by a suitable means such as laser marking for insertion depth and rotation reference, for example in 1 centimeter increments, to assist in device positioning. For example, in the embodiment shown in FIG. 2 shown, the length of the probe tubing is preferably in the range of 45 to 65 cm, and most preferably in the range of 52 cm.

Figure 3:
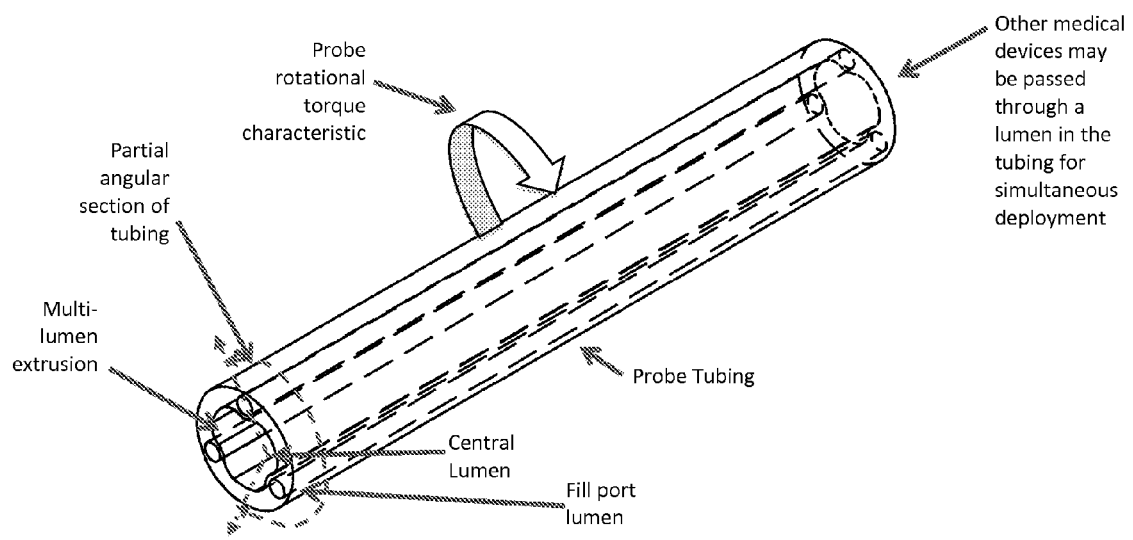
FIG. 3 illustrates a perspective view of an embodiment of the esophageal probe tubing profile.

With reference to FIGS. 2 and 3, in some embodiments the tubing consists of a multi-lumen extrusion with a central lumen for the routing of electrical conductors and sound, and at least one additional internal lumen for the conduction of balloon inflation methods. In further embodiments, the probe tubing comprises components which allow operator control of the probe rotation around an axial axis in the esophagus while maintaining the longitudinal flexibility appropriate for insertion in the patient. The torsion characteristics are preferably in the range of 100-400 gram(force)*cm per degree per cm length of tubing and most preferably in the range of 200-300 gram(force)*cm per degree per cm length of tubing. Torsion characteristics are also a function of the multi-lumen tubing profile shown in FIG. 3 and of the stiffness of the tubing material, which in some embodiments comprise a biocompatible flexible thermoplastic elastomer of, for example, PEBAX 4033 SA01 (Arkema Inc., King of Prussia, Pa., USA) a thermoplastic elastomer with a shore D hardness of 42, and an outer diameter of 8.1 mm. In other embodiments, stiffening elements e.g., braiding of metal rods or wires are extruded beneath the outer surface of the tubing, increasing the torsion force to at least 300 gram(force)*cm per degree per cm length of tubing.

In further embodiments, a lumen, preferably a central lumen of the tubing is open on both ends to facilitate the passage of nasogastric or orogastric tubes or other devices which are deployed simultaneously by means of passage through the probe. A suitably sized internal lumen is in the range of 4 to 8 mm in diameter, and preferably is in the range of at least 5 to 6 mm diameter. Such an opening is also suitable for the passage of a miniature profile TEE device (e.g., 15 French size, ~5 mm diameter).

In a still further embodiment, tubing is in the form of a partial angular section and length to comprise a "carrier" element, upon which the sensor elements are mounted. In some embodiments, the carrier element is attached to other medical devices such as an esophageal stethoscope, TEE device, or orogastric or nasogastric tube, to use the probe simultaneously with the other devices. In some embodiments, a carrier uses a partial angular section of tubing containing sensor elements, wherein the partial angular section of tubing is an angled section in the range of 150 to 300 degrees, or in the range of 180 to 240 degrees, with a length in the range of 2.5 to 8 cm, or in the range of 3 to 6 cm. In some embodiments, a carrier is constructed to fit to or mate to specific devices.

Probe Sensor

Figure 4:
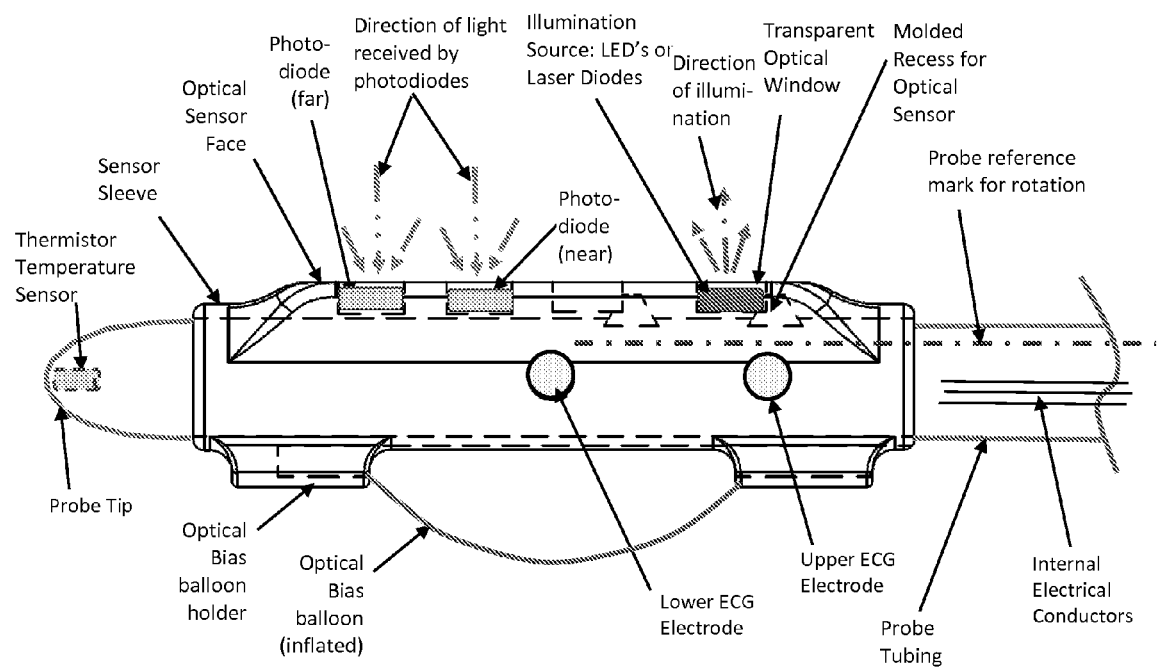
FIG. 4 illustrates a side view of an embodiment of probe sensor elements.

As shown in FIG. 4, in one embodiment the probe comprises a molded sleeve which encircles the probe tubing and contains a multiplicity of sensor elements used to measuring physiological parameters. In some embodiments, esophageal sensors may incorporate a temperature sensor for the measurement of core temperature, or ECG electrodes, for the measurement of esophageal ECG rhythms. In certain embodiments, a thermistor temperature sensor is located internally in the probe's distal tip, and an upper ECG electrode and lower ECG electrode are deployed. In preferred embodiments, sensor elements communicate appropriately to internal electrical conductors in the center lumen of the probe tubing.

In some embodiments, pulse oximeter sensor elements are configured on a single outward sensor face in a co-planar arrangement. In some embodiments, the sensor elements are positioned within recesses on the sensor face and interface to the environment opposite the sensor face via optically transparent windows. In other embodiments, a pulse oximeter illumination source is positioned at a specified location on the sleeve. In preferred embodiments, at least two solid state light sources, comprising either light emitting diodes (LED's) or laser diodes (LD's) are sequentially illuminated, thereby directing their illumination outward from the face. For example, in some embodiments, a red LED with center wavelength in the range of 655 to 665 nm and preferable in the range of 658-662 nanometers, and an infrared LED with center wavelength in the range of 895 to 920 nanometers and preferably in the range of 904 to 910 nanometers is used, with a radiant optical power in the range of 1 to 5 milliwatts under a test current of 20 mA, most preferably in the range of 2.0 to 3.5 mW under the stated conditions. In other embodiments, other wavelengths, wavelength ranges or tolerances, or combinations of wavelengths used in pulse oximetry are used as determined by requirements associated with a specific pulse oximeter module type.

In one embodiment, at least one detector to receive light is used for pulse oximetry. In other embodiments two detectors are used e.g., one proximal detector and one distal detector with respect to the position of the illumination source. The detectors receive light that approaches the sensor face as shown in the received light direction. In some embodiments, the detectors are located at a distance in the range of 1 to 4 centimeters from the illumination source as measured by the component optical center to center distance. In other embodiments, they are located at 1.75 centimeters distance for the proximal and 2.5 centimeters for the distal detector. Either detector is suitably employed individually by means of connection to a pulse oximeter module, or both detectors simultaneously by electrical simultaneous connection. In one embodiment, the detector type is a silicon PIN photodiode with an active area of 7.0 square millimeters. In some embodiments, other detector areas are used. In some embodiments, each sensor element communicates appropriately to an internal electrical conductor in the central lumen of the probe tubing.

In one embodiment, a movable element to position the optical sensor face in predetermined proximity to the target site to be measured is used. As shown in FIG. 4, and with reference to FIG. 2, in some embodiments, an optical bias balloon is located on the opposite side of the probe from the optical sensor face. In some embodiments, the optical bias balloon is filled by the introduction of air or a liquid such as water or sterile saline 0.9% by means of a syringe into the bias balloon fill port on the bias fill tube. For safe use, in some embodiments the optical bias balloon is deployed in the deflated state during insertion or retraction of the probe, and subsequently inflated during measurement sequences.

In some embodiments, the diameter of the probe without balloon is in the range of 5.0 to 13 millimeters in diameter, and preferably in the range of 8.0 to 11 millimeters in diameter in further embodiments. In certain embodiments, smaller diameters are used for nasopharyngeal introduction instead of oropharyngeal introduction. In some embodiments, the natural volume of the optical bias balloon is in the range of 1.5 to 4.0 cubic centimeters (fluid), and preferably in the range of 2.0 to 3.0 cubic centimeters, provided that a maximum safe diameter for deployment is under a total effective diameter of 20 to 22 millimeters including probe, a specified upper safe limit for deployment in a normal healthy esophagus. In some embodiments, the balloon material is specified as a suitable biocompatible material such as a flexible urethane elastomer, or preferably Pellethane 2363-90A, Polyurethane Elastomer (Lubrizol Corporation, Wickliffe, Ohio, USA).

In some embodiments, a pressure sensor is employed to sense the inflation pressure of the optical bias balloon for safe deployment, particularly to sense over-pressure in the presence of an esophageal anomaly such as a stricture, in order to prevent damage to the esophagus. Sensors comprise any suitable pressure transducer such as a manometer for use with air, or a fluid transducer with fluids. In one embodiment, the pressure is continuously monitored to ascertain the safe deployment of the balloon. Normal resting pressures within the esophagus are in the range of 0 to 40 mmHg and increase to 80 to 150 mmHg during swallowing. A static pressure in the range of 40 mmHg to not exceeding 100 mmHg is associated with an inflated bias balloon and more preferably in the range of 60 mmHg to not exceeding 80 mmHg. In some embodiments, the balloon is periodically deflated to allow the local esophageal tissue to normally perfuse with blood for a brief recovery time. In other embodiments, a recovery cycle is used wherein the balloon is periodically deflated in the range of 15 seconds to 5 minutes for every 10 minutes of inflation time, or preferably in the range of 30 seconds to 1 minute for every 10 minutes of inflation time. Other duty cycles are possible. In further embodiments, optical bias balloon inflation and deflation is initiated manually or automatically.

Figure 5:
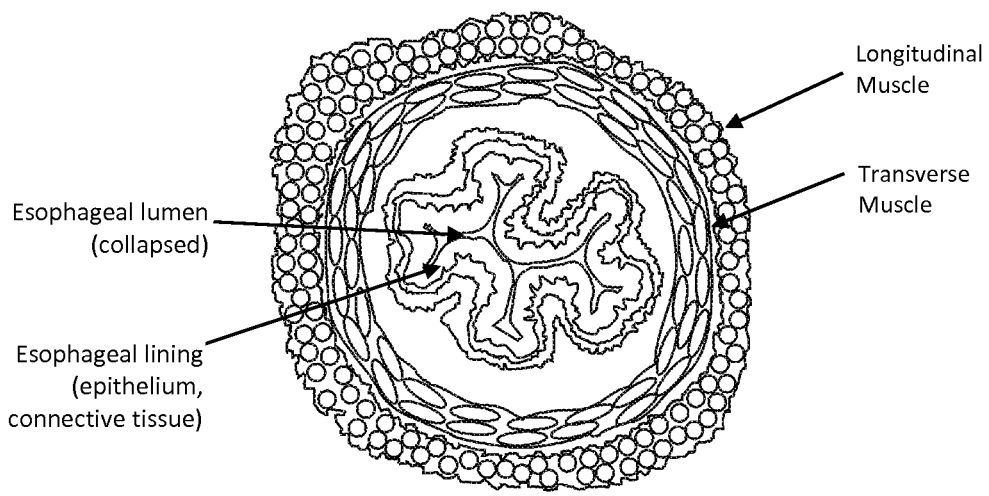
FIG. 5 illustrates a cross sectional anatomical view of the esophagus.
Figure 6:
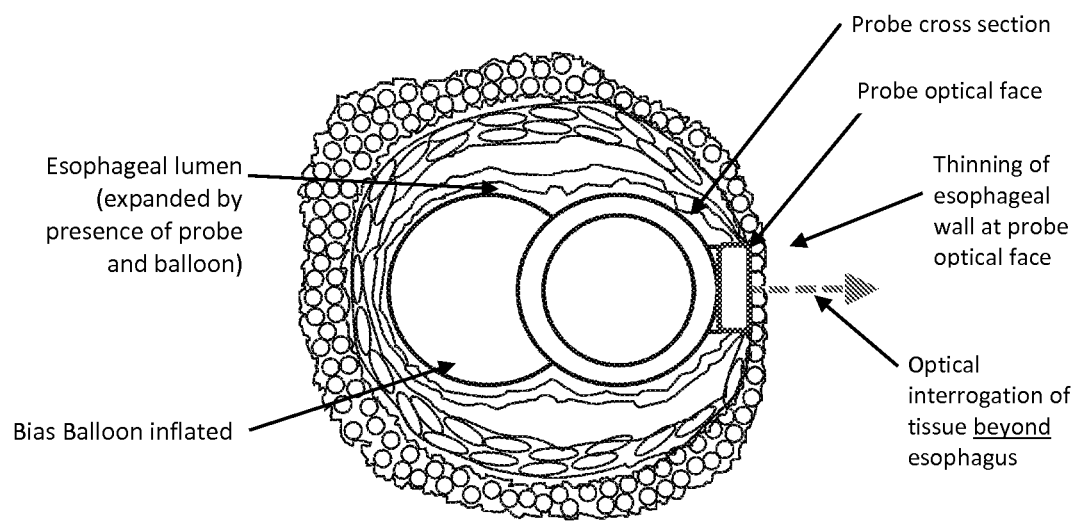
FIG. 6 illustrates a cross sectional view of a probe deployed with bias balloon to thin the esophagus.

As shown in FIG. 5 and FIG. 6, in some embodiments, expansion of the optical bias balloon increases the effective diameter of the probe, thereby impinging upon the esophageal tissue in a manner which locally decreases the effective thickness of the esophagus at the site of the optical measurement. Thus, the purpose of balloon inflation is not solely to maintain optical contact to the esophageal wall but also to locally thin the esophageal wall by means of gentle compression upon the readily deformable structures of the esophageal epithelium and longitudinal and transverse muscles in order to facilitate the measurement of blood-filled structures beyond the esophagus.

Physiological Locations

The proximity of the esophagus to the heart and major cardiac vessels in humans and primates provides an opportunity for interrogation of major blood-filled vessels and cardiac chambers for oxygen saturation. FIGS. 7 to 10 illustrate anatomical sections which illustrate the relationships in adult human patients.

Figure 7:
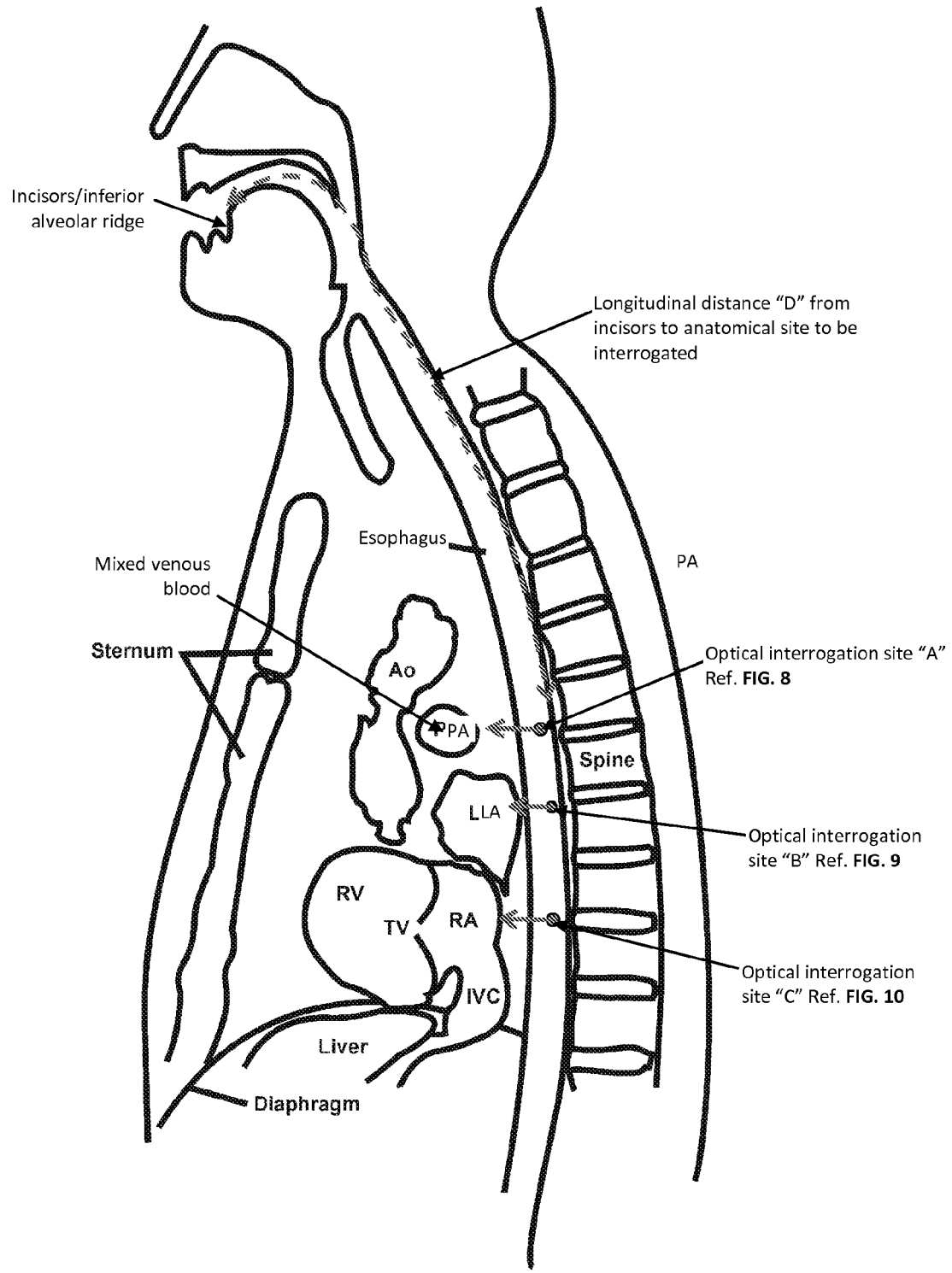
FIG. 7 illustrates a longitudinal midline anatomical view showing the proximity of the esophagus to blood-filled structures of the chest.

FIG. 7 is a longitudinal midline anatomical section view which shows the esophagus in proximity to the spine. The relationship between the esophagus and the pulmonary artery corresponds to optical interrogation site "A" directed in an anterior direction from the esophagus, for which the distance "D" from the incisors is generally in the range of 25-32 cm, and more preferably in the range of 26-31 cm. The pulmonary artery is a blood-filled vessel which conducts mixed venous blood, which integrates the most venous (oxygen depleted) blood in the body, and therefore with a low measurable oxygen saturation.

In another view in FIG. 7, the relationship between the esophagus and the left atrium corresponds to an optical interrogation site "B" directed in an anterior direction from the esophagus, for which the distance "D" from the incisors is generally in the range of 27-34 cm, and more preferably in the range of 28-33 cm. The left atrium is a blood filled cardiac chamber which conducts arterial blood with a high measurable oxygen saturation.

In yet another view in FIG. 7, the relationship between the esophagus and the right atrium corresponds to an optical interrogation site "C" directed in an anterior direction from the esophagus, for which the distance "D" from the incisors is generally in the range of 31-40 cm, and more preferably in the range of 33-38 cm. The right atrium is a blood filled cardiac chamber which conducts central venous blood, which therefore has a low measurable oxygen saturation.

Figure 8:
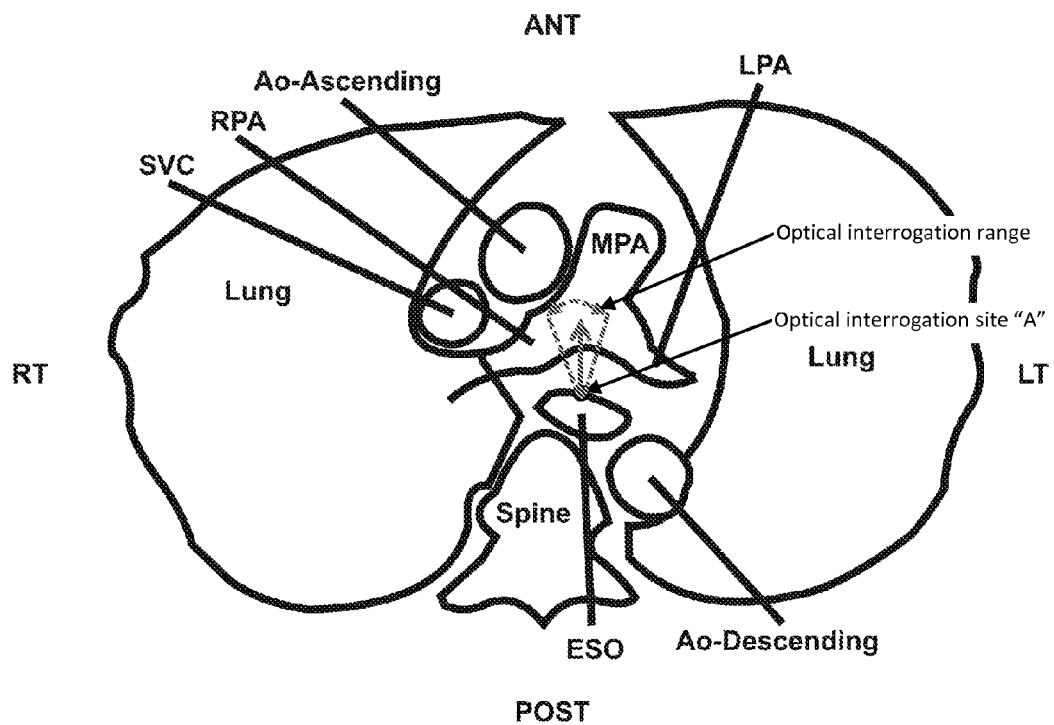
FIG. 8 illustrates a proximal transverse anatomical view at the level of the pulmonary artery bifurcation.

FIG. 8 shows a transverse anatomical section view at the level of the right pulmonary artery corresponding to the same optical interrogation site "A" as shown in FIG. 7, and similar anatomical relationships from a transverse direction. The relative locations of the esophagus to the spine, descending aorta, ascending aorta, superior vena cava, and lung are also illustrated. The distance of the right pulmonary artery from the esophagus coincident with the line of the optical interrogation site "A" is generally in the range of 0.5-2.0 cm and most preferably in the range of 1.0-1.5 cm. The preferred angular direction of optical interrogation site "A" towards the right pulmonary artery is within the range of ±20 degrees from the anterior direction (anterior is zero degrees by convention), and most preferably in the range of less than ±10 degrees from the anterior direction.

Figure 9:
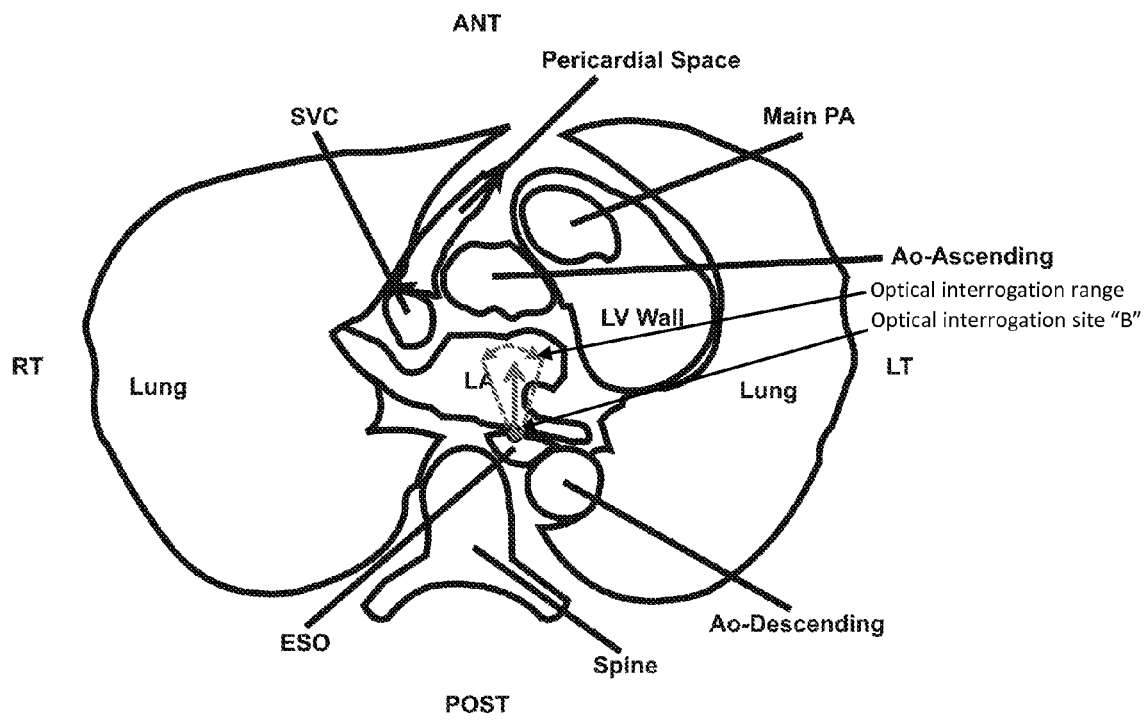
FIG. 9 illustrates a midline transverse anatomical view at the level of left atrium.

FIG. 9 shows a transverse anatomical section view at the level of the left atrium corresponding to the same optical interrogation site "B" as shown in FIG. 7, and similar anatomical relationships from a transverse direction. The relative location of the esophagus to the spine, descending aorta, ascending aorta, superior vena cava, left ventricular wall, and lung are also illustrated. The distance of the left atrium from the esophagus coincident with the line of the optical interrogation site "B" is within the range of ≤2 cm and most preferably in the range of 0.5-1 cm. The angular direction of optical interrogation site "B" towards the left atrium is in the range of ±20 degrees from the anterior direction and most preferably in the range of less than ±10 degrees from the anterior direction.

Figure 10:
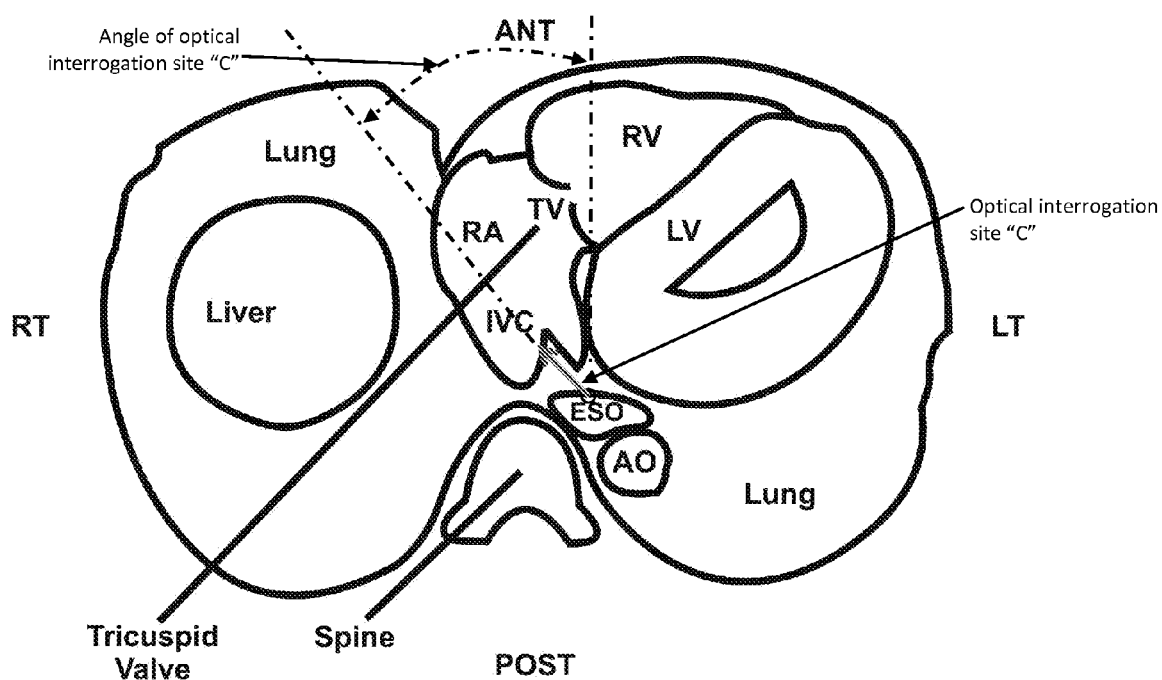
FIG. 10 illustrates a distal transverse anatomical view at the level of right atrium, inferior vena cava.

FIG. 10 shows a transverse anatomical section view at the level of the right atrium corresponding to the same optical interrogation site "C" as shown in FIG. 7, and similar anatomical relationships from a transverse direction. Relative location of the esophagus to the spine, descending aorta, left ventricular wall, inferior vena cava, and lung are also illustrated. The distance of the right atrium from the esophagus coincident with the line of the optical interrogation site "B" is within the range of 1.0-3.0 cm and most preferably in the range of 1.5-2.0 cm. The angular direction of optical interrogation site "C" towards the left atrium is within the range of 30 to 60 degrees to the right anterior direction and more preferably in the range of 40 to 50 degrees to the right of the anterior direction.

Distances and angles specified above for FIGS. 8-10 are dependent upon the height and other individual anatomical characteristics and variations, and thus are representative of values observed in a typical adult human patient. The anatomical sites for measurement described above are exemplary of the measurement principles of the described technology, and are not intended to limit the scope of anatomical sites which are thus interrogated. In some embodiments, a method is provided to facilitate location of target measurement sites, i.e., venous and arterial blood-filled structures as described in FIGS. 7-10, without prior knowledge of their exact longitudinal and angular locations or relative anatomical relationships in a specific patient.

Figure 11:
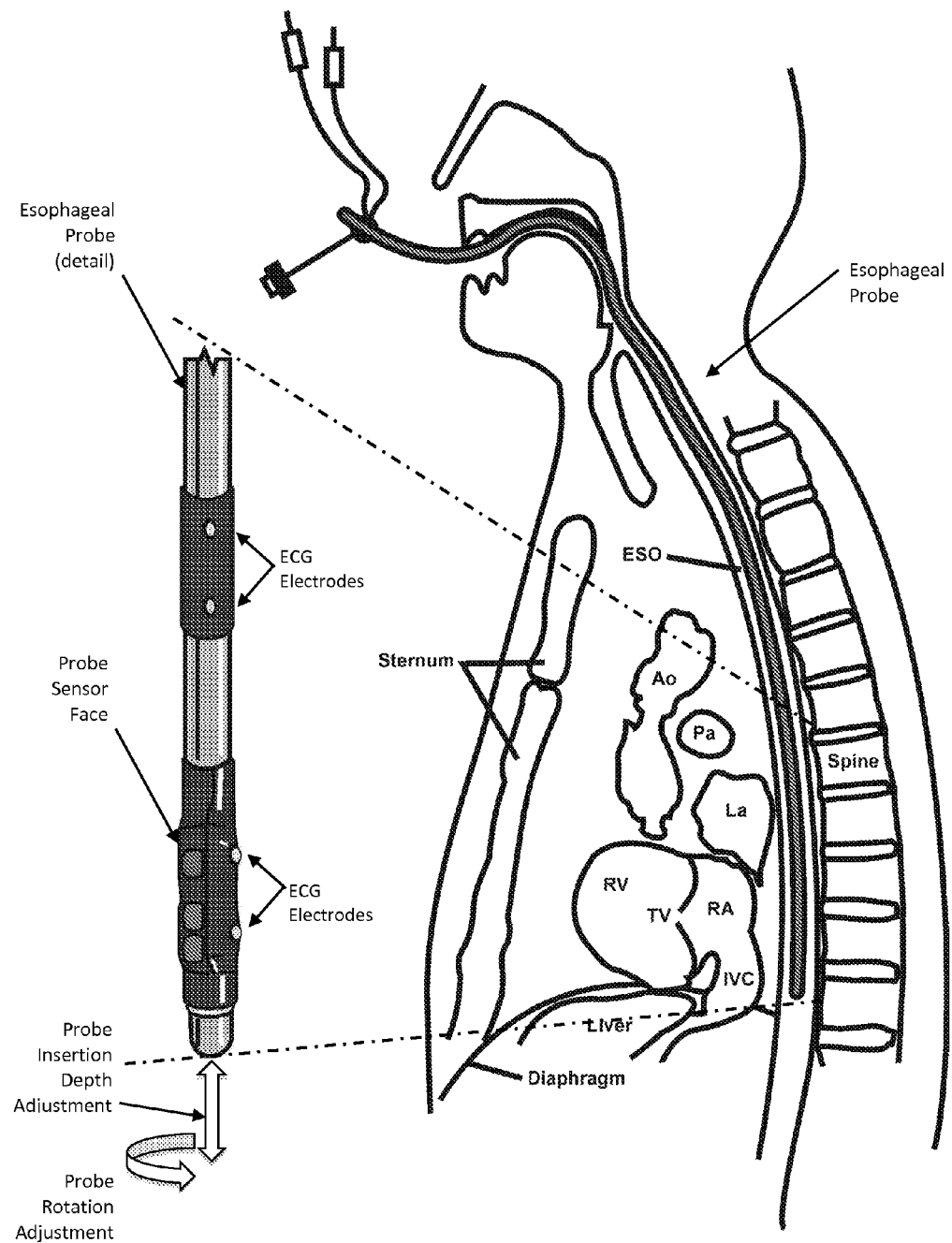
FIG. 11 illustrates a longitudinal midline anatomical view with an esophageal probe in position.

With reference to FIG. 11, in some embodiments a probe is inserted into the esophagus and is positioned to interrogate the oxygen saturation of various anatomical locations by means of adjustment of the probe's insertion depth and rotation to direct the probe optical face in various states of rotation. In this manner it is possible to direct the probe optical face to target sites of interest, which may include the right atrium, inferior vena cava, left atrium, pulmonary artery, or other target structures as previously discussed.

Figure 20:
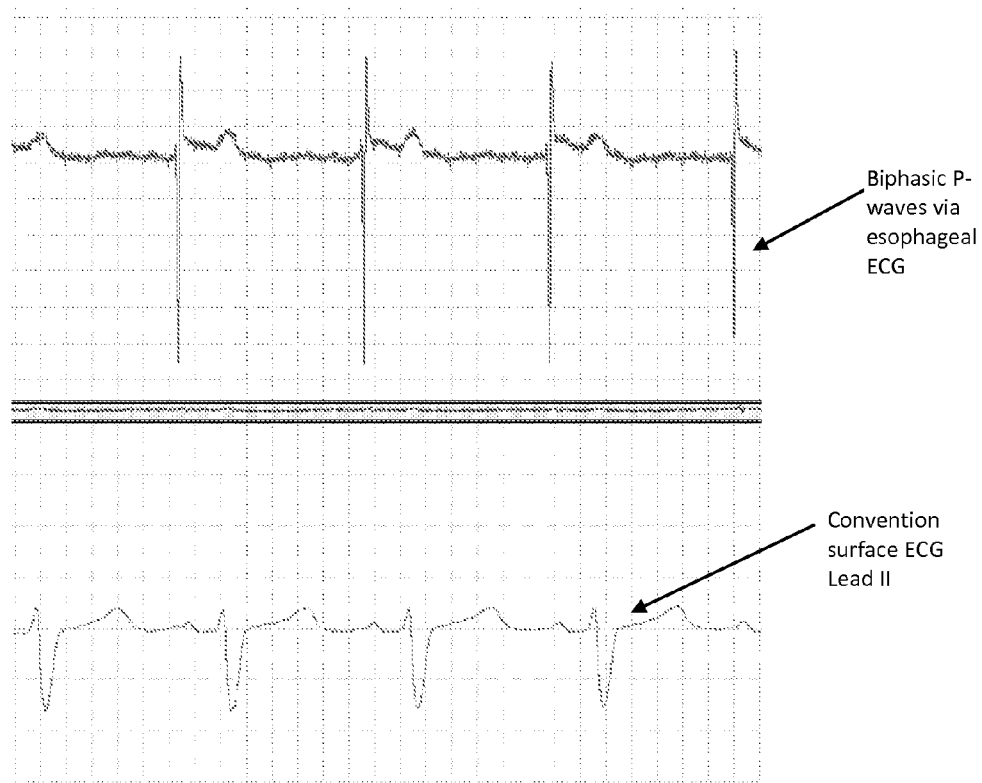
FIG. 20 illustrates an esophageal ECG waveform (upper trace) with biphasic P-waves obtained in proximity to the left atrium, and the LEAD II surface ECG waveform (lower trace).

In some embodiments, esophageal ECG electrodes provide signals which are used to assist in probe positioning, such as atrial P-waves (Atlee (U.S. Pat. Nos. 5,370,679, 5,394,880) and Hickey (U.S. Pat. No. 5,570,671)). With reference to FIG. 20, in some embodiments the amplitude and polarity of the P-waves is obtained by an ECG electrode pair as an indicator of an electrode pair's proximity to the left atrium. Use of signals from ECG electrodes in combination with the methods herein thus augment the ability to locate specific target measurement sites by providing a reference signal indicative of relative position of the probe to the left atrium. FIG. 11 shows exemplary ECG electrode pairs in two locations on a probe suitable for obtaining ECG waveforms.

Figure 12:
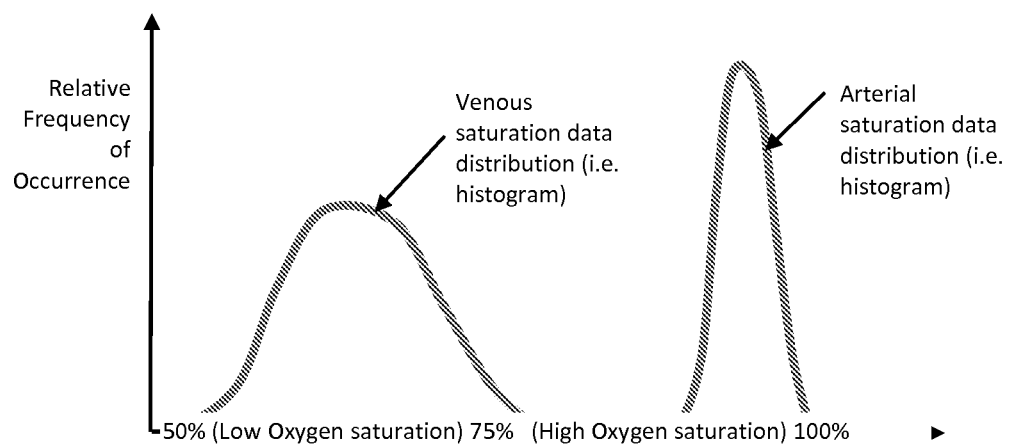
FIG. 12 illustrates a histogram showing venous and arterial oxygen saturation measurements in proximity to the esophagus.

As shown in FIG. 12, different target structures contain markedly different levels of oxygen saturation corresponding to their venous or arterial origins, respectively. Measurements obtained by positioning the probe and at least one sensor in proximity to blood-filled structures provide oxygen saturation values representative of either or both venous oxygen saturation components and arterial oxygen saturation components arising from the structures interrogated.

In some embodiments, the relative frequency of the occurrence of oxygen saturation values obtained plotted against defined intervals of oxygen saturation, provides a histogram of oximetry values which is obtained by sensor and measurement system in accordance with the deployment of the technology described herein. For example, a histogram is defined for the oxygen saturation interval of 50 percent oxygen saturation to 100 percent oxygen saturation in 1 percent increments, spanning a venous to arterial oxygen saturation range, wherein 50 to 80 percent oxygen saturation is most often associated with venous blood, and 90 to 100 percent oxygen saturation is most often associated with arterial blood.

In some embodiments, a histogram plot depicting the relative frequency of occurrence of oxygen saturation values shows a histogram distribution with a greater relative frequency of values associated with lower oxygen saturation measurements when in the presence of venous structures, and, conversely, shows a histogram distribution with a greater relative frequency of values associated with higher oxygen saturation measurements in the presence of arterial structures. Thus, in some embodiments, a histogram of the distribution of oxygen saturation values obtained from the probe and measurement system is employed to assist in distinguishing venous and arterial structures. In some embodiments, a method for first obtaining and subsequently using a histogram that comprises a plot of relative frequency of occurrence of oxygen saturation values which span the venous to arterial oxygen saturation range is used to identify the position of a particular blood-filled structure, optimize the placement of the probe in proximity to that structure, and provide a method to assess the ongoing quality of the measurement.

Figure 13:
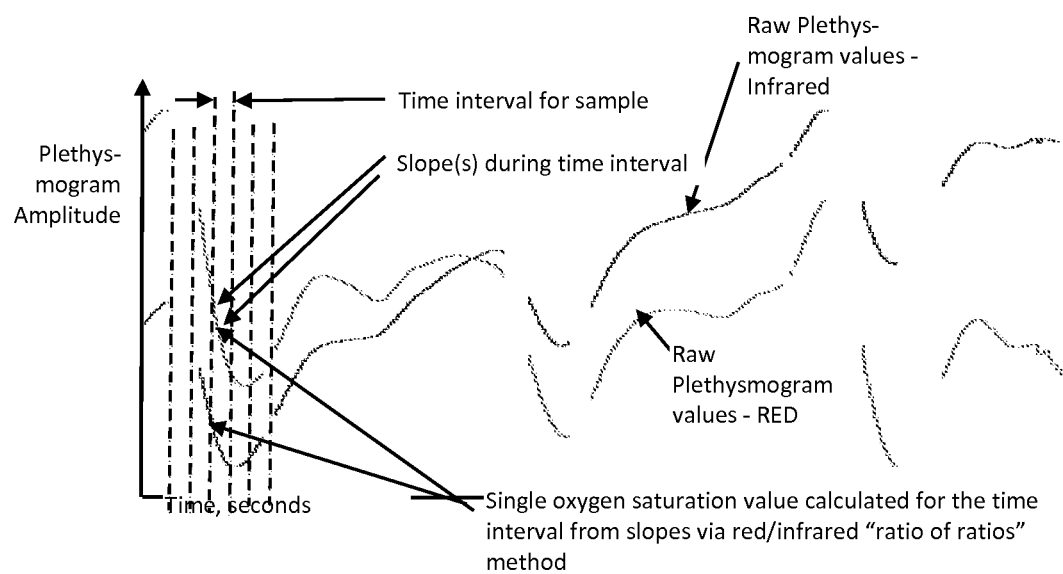
FIG. 13 illustrates an exemplary photoplethysmogram.
Figure 14:
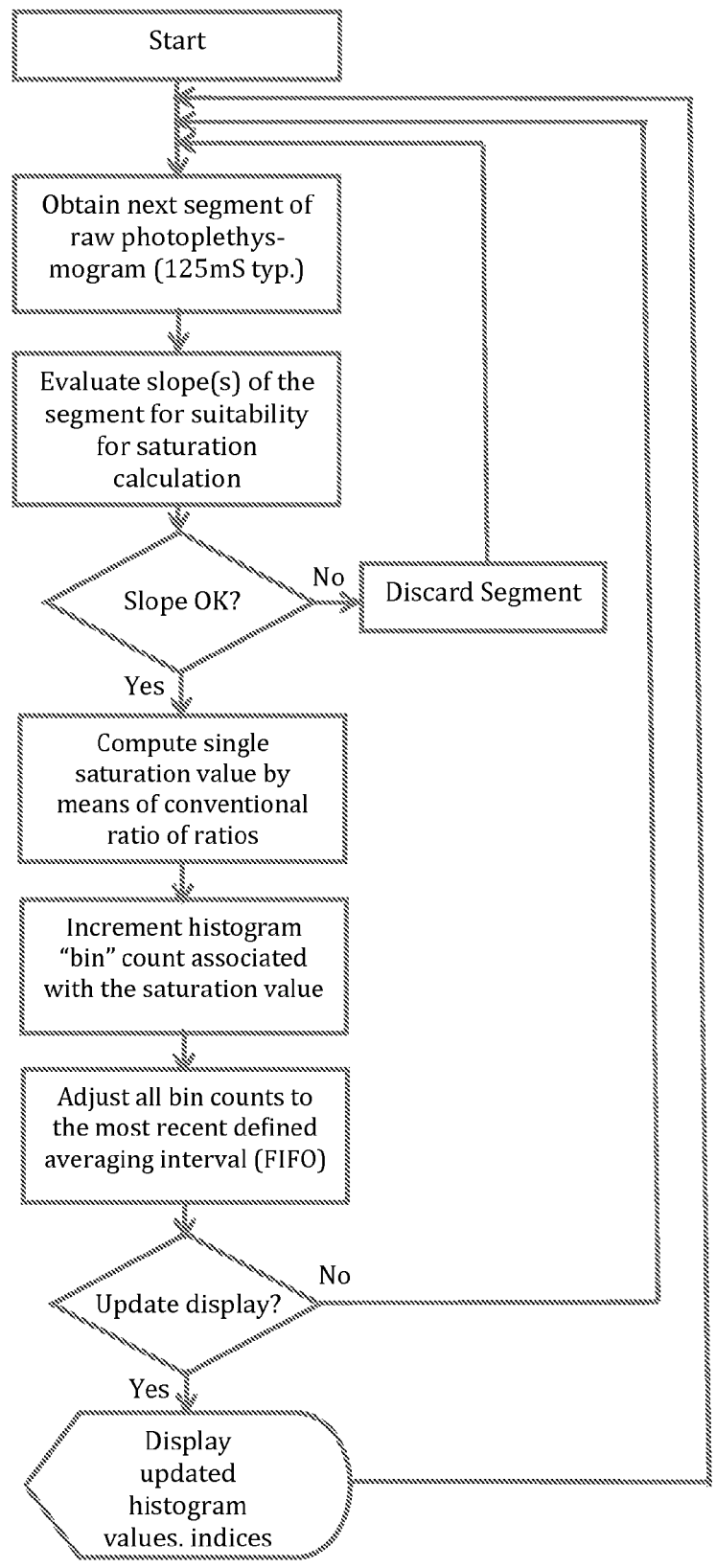
FIG. 14 illustrates a flowchart of a method used to generate an oximetric histogram.

With reference to a FIGS. 13 and 14, in some embodiments a method of obtaining a histogram for this purpose is provided that comprises operations described herein. In some embodiments, the operations are performed on the data stream from a commercially available pulse oximeter module configured to output digitized time-varying photoplethysmogram values corresponding to the amplitude of photodetector light measured for each illumination source. In some embodiments, deployed pulse oximeter modules, including the examples referenced herein, the data stream corresponds to the photoplethysmograms obtained with red and infrared light emitting diode (i.e. LED) illumination of the tissue. In other embodiments, other illumination sources, including a plurality of LEDs or laser diodes at various wavelengths in the visible and infrared spectrum, are used. In some embodiments, methods to generate a histogram of the technology described herein include the following steps:

0. (Initialization step) Define a set of bins representing oxygen saturation in percent, which are initially set to zero prior to measurement. To provide suitable resolution for the histogram, in some embodiments the bin resolution is in the range of 0.5 percent oxygen saturation to 10 percent, in other embodiments in the range of 1 percent to 5 percent resolution and in further embodiments in the range of 1 percent to 2 percent resolution. In some embodiments, the displayed range of oxygen saturations for venous and arterial blood are in the range of 0% to 100% oxygen saturation with, for example, 100 bins of 1 percent oxygen saturation width each spanning the oxygen saturation range of 0 percent to 100 percent. Other sub-ranges are possible. For example, a patient may have measured mixed venous oxygen saturation in the range of 40% to 80%, or approximately 75% in a healthy patient.

151. Sample successive segments of the raw photoplethysmogram waveforms for each wavelength. In some embodiments, the segment interval are in the range of 20 milliseconds to 250 milliseconds; in other embodiments they are in the range of 50 to 150 milliseconds; in further embodiments they are in the range of 100 to 125 milliseconds.

202. Evaluate the slope of a selected segment to determine if that segment is to be accepted for oximetric calculation based upon the acceptability criteria of the slopes for calculation. In some embodiments, an acceptable minimum slope is in the range of 120 to 400 counts per sample segment. In other embodiments, an acceptable minimum slope is in the range of 240 to 300 counts per sample segment using a resolution of 65,536 digitized count values for the plethysmogram, or in the range of 0.2 percent to 0.6 percent of the total magnitude of the plethysmogram in some embodiments, or preferably 0.35 percent to 0.45 percent of the total magnitude of the plethysmogram in still further embodiments.

Calculate a single oxygen saturation percent value using the conventional ratio of ratio method known in the art of oximetry, specifically to calculate functional arterial oxygen saturation:

$$\text{Ratio of Ratios: } r \sim \frac{\ln\left(\frac{RedAC}{RedDC}\right)}{\ln\left(\frac{InfraredAC}{InfraredDC}\right)}$$

The AC component is defined herein as the amplitude of the pulsatile component arising from blood pulsation, and the DC component is defined herein as the amplitude of the non-pulsatile component arising from skin, epithelium, structural tissue, bone, etc.

A ratio, r, of 0.5 represents approximately 100% oxygen saturation, a ratio of 1.0 represents approximately 82% oxygen saturation, while a ratio of 2.0 equates to an oxygen saturation which approximates 0%. Thus the relationship of saturation to the ratio, r, sometimes called the r-curve, is non-linear. In practice, the r-curve representing the relationship of the saturation to the ratio, r, is empirically adjusted in accordance with a clinical data, to maximize accuracy for the defined sensor configuration, which uses specific red and infrared wavelengths. In some embodiments, this is accomplished by establishing a look-up table which maps saturation values to r values. Use of a lookup table (instead of, for example a logarithmic ratio) also improves computation speed during use. In some embodiments, clinical or otherwise empirically obtained mathematical adjustments to the calculation are provided.

3. In accordance with a method of the histogram calculation, increment the value of the "bin" associated with the percent oxygen saturation value obtained. For example, a calculated single oxygen saturation value of 78% would cause the bin count associated with the value 78 to be increased by one, and a calculated single oxygen saturation value of 94% would cause the bin count associated with the value 94 to be increased by one count. In some embodiments, the increment value is a value other than 1 and is used consistently, i.e., for all counts.

254. Repeat steps 1-4 above to accumulate values and load the histogram bins with the counts of oxygen saturation (i.e., relative frequency of occurrence) vs. oxygen saturation per the defined bins. The iterative accumulation of counts for each of the respective bins is a representation of the relative frequency of occurrence (i.e., counts per bin) of measured oxygen saturation values.

305. Display a real-time histogram graphic representation of relative frequency of occurrence (i.e., counts per bin) vs. oxygen saturation.

6. Update the histogram graphic representation periodically to represent all values in the most recent defined averaging time, with the option to select various averaging time intervals. In some embodiments, suitable averaging time intervals is in the range of 5 to 300 seconds and preferably in the range of 10 to 60 seconds and most preferably in the range of 5 to 15 seconds for interactive probe positioning with feedback to the operator. In some embodiments, once a probe has been suitably positioned at a target measurement site, a longer averaging interval in the range of 20 to 60 seconds is used.

7. In some embodiments, in addition to the displayed oxygen saturation distribution, a signal quality index is reported comprising the ratio of suitable measurements obtained to the measurements attempted for the most recent averaging interval. This index provides a general assessment of the measurement quality at the specified location, and assists the operator in assessing or determining the suitability of current probe location. In some embodiments, the named ratio or quality index is in the range of 0.10 to 1.00 and preferably in the range of 0.50 to 1.00 and most preferably in the range of 0.70 to 1.00 for measurements providing suitable physiological data. Other representations of this index are possible, as raw count or percentage or color, for example.

In some embodiments, as described above, a displayed histogram provides a visual representation of the valid/accepted oxygen saturation measurements for the current averaging interval and permits operator assessment of the fundamental oxygen saturation, which will be visually associated with the region of highest magnitude of the histogram. In some embodiments, additional parameters/indices are computed and displayed to assist assessment of histogram, including oxygen saturations associated with the peak value of the histogram and the centroid of the histogram. In some embodiments, calculation of the width of the histogram in oxygen saturation units via standard deviation or full width half maximum (FWHM) calculation provides information with regard to, for example, venous mixing at a venous measurement site. The description of the histogram methods, compositions and systems above are examples of the described technology, and are not limited to the embodiments described above. Additionally, in some embodiments, other parameters and indices of oximetry are measured and reported, including, for example for pulse modulation and pulse rate. The method described of obtaining, calculating and displaying a histogram allows a user to readily visualize the distribution of oxygen saturation at a specific anatomic site and, using feedback provided by a visual display, to beneficially position the probe to optimize, for example, the venous signal from a venous structure.

Figure 15:
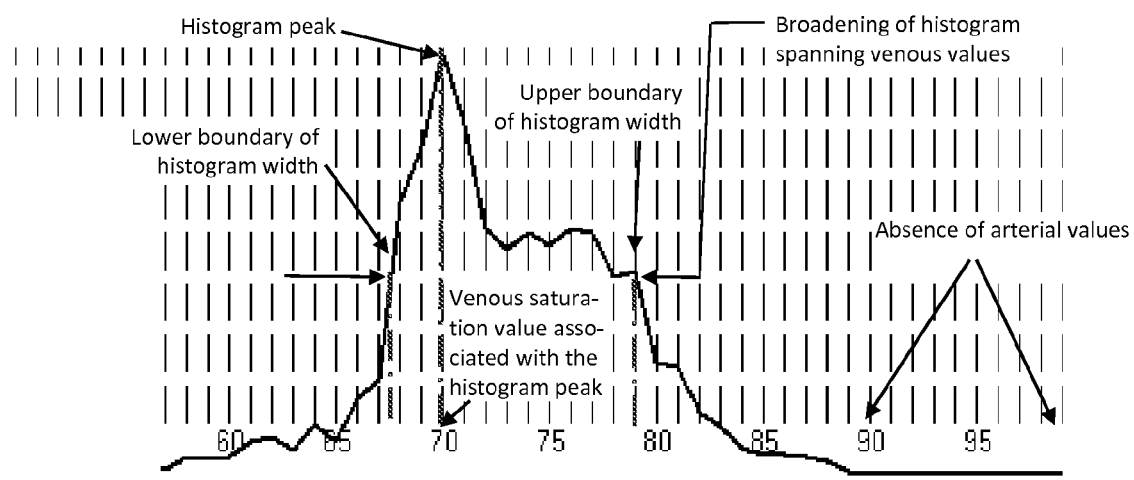
FIG. 15 illustrates a histogram of mixed venous oxygen saturation values with a probe at the level of the right branch of the pulmonary artery.

FIG. 15 shows the histogram of mixed venous oxygen saturation values obtained with a probe at the right pulmonary artery, a venous blood-filled structure. This histogram is illustrative of characteristics of a venous measurement site including an oxygen saturation value coinciding with the peak of the histogram which is consistent with values expected from a venous blood-filled structure, in the range of 85 percent oxygen saturation or lower, or in the range of 60 to 80 percent oxygen saturation, depending on the physiology and medical condition of an individual patient. A further characteristic of a venous histogram is a broadening of the histogram about either side of the peak, for example, at half the maximum peak value, such that a lower boundary value and upper boundary value both exist, and wherein the oxygen saturation values enclosed by the lower and upper boundary values span values associated with venous blood-filled structures and wherein oxygen saturation values bracketed by the lower and upper boundaries span a range of 5 to 15 oxygen saturation percent units. A further characteristic of a venous histogram is the absence of values associated with arterial oxygen saturation, that is, of values above 85 percent oxygen saturation, or at and above 95 percent oxygen saturation, depending on the physiology and medical condition of an individual patient. In certain embodiments, the blood oxygenation saturation of structures filled with venous blood is measured during non-systolic intervals thereby reducing the contribution of signals arising from arterial pulsations In some embodiments, the oxygen saturation value associated with the peak of the histogram is reported as the oxygen saturation measurement value obtained from a venous blood-filled structure, and the oxygen saturation values associated with the upper and lower FWHM (full with half maximum) boundaries reported as ancillary oxygen saturation values, with the difference between the upper and lower FWHM (full with half maximum) boundaries reported as an ancillary oxygen saturation range. Ancillary oxygen saturation values may provide additional data useful either in clinical interpretation (e.g., information on the magnitude of venous mixing), or in an ongoing assessment of the quality of the measurement (e.g., broadening or narrowing of the oxygen saturation range as an indicator of alignment).

Figure 16:
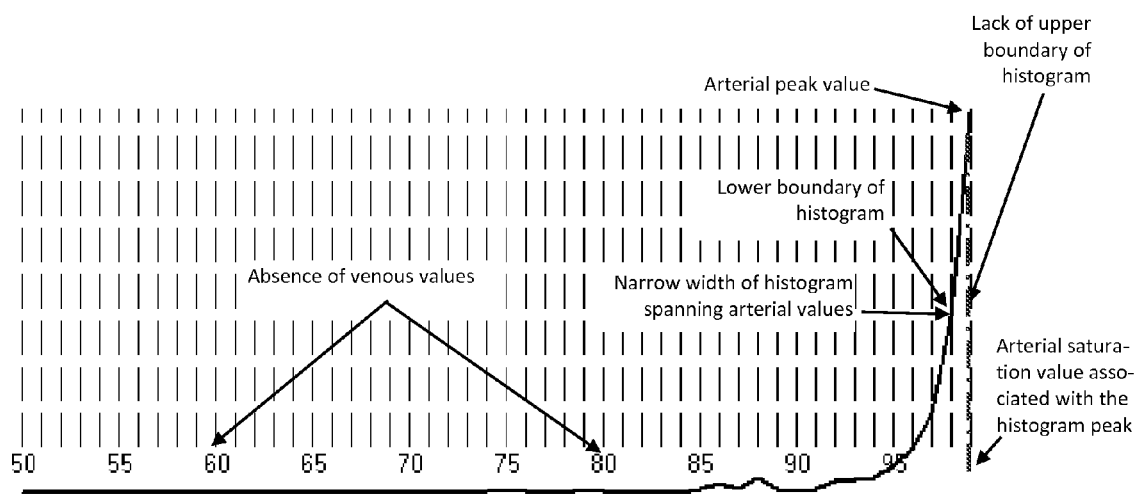
FIG. 16 illustrates a histogram of arterial oxygen saturation values with a probe at the level of the left atrium.

FIG. 16 shows a histogram of arterial oxygen saturation values obtained with the probe at the left atrium, an arterial blood-filled structure. This histogram is illustrative of characteristics of arterial measurement sites including an oxygen saturation value coinciding with the peak of the histogram which is consistent with values expected from an arterial oxygen saturation measurement, in the range of 85 percent oxygen saturation or higher, or in the range of 95 percent oxygen saturation and above, depending on the physiology and medical condition of an individual patient. A further characteristic of an arterial histogram is a broadening of the histogram, for example at half the maximum peak value, such that a lower boundary value exists and wherein the upper boundary value may or may not exist i.e., the effective upper boundary is coincident with the upper oxygen saturation value that can be measured, effectively 100 percent oxygen saturation units, and wherein the oxygen saturation values bracketed by the lower and effective upper boundaries span values associated with arterial oxygen saturation measurements, and wherein the oxygen saturation values bracketed by the lower and effective upper boundaries span a range of 2 to 5 oxygen saturation percent units. A further characteristic of an arterial histogram is a general absence of values associated with venous oxygen saturation, and again depending on the physiology and medical condition of an individual patient. In further embodiments, a percent modulation of at least 5% is contributed by a pulsatile (i.e., AC) portion of a measured signal compared to a total signal otherwise arising from non-pulsatile tissue sources.

Figure 17:
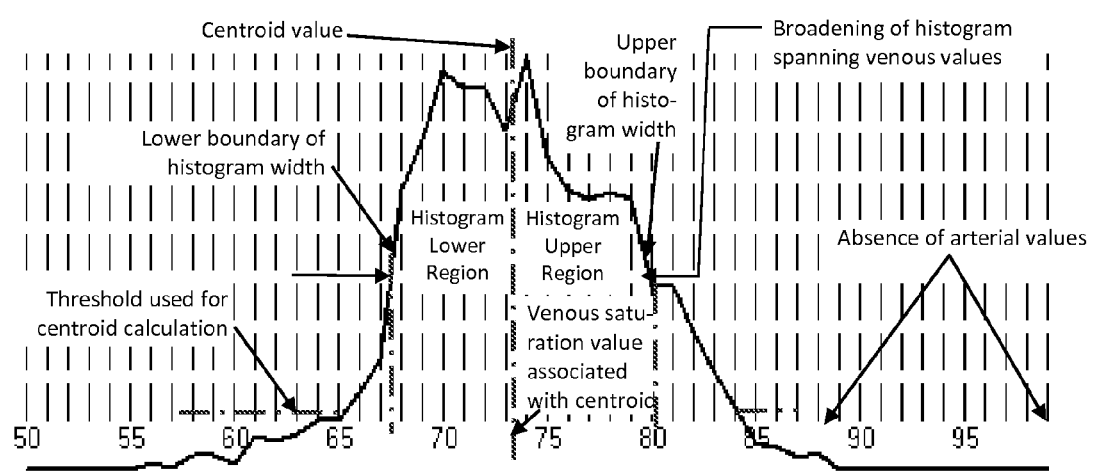
FIG. 17 illustrates a histogram of central venous oxygen saturation values with a probe at the level of the right atrium.

FIG. 17 shows the histogram of central venous oxygen saturation values obtained with the probe at the right atrium, a venous blood-filled site. The features of a venous measurement site as applied to the venous measurement site for FIG. 15 are similarly applicable. FIG. 17 is illustrative of characteristics of a venous measurement site including an oxygen saturation value corresponding with the centroid value of the histogram wherein the centroid is defined as the value wherein the histogram is divided into equal areas i.e., wherein a histogram lower region and upper region are effectively bisected such that they define equal areas, or a numerical equivalent comprising two equal histogram sections in which the sum of the histogram bin sections is equal. In some embodiments, a centroid value is obtained by numerical interpolation of a set of summed histogram values. The centroid value so obtained is interpolated within a boundary of a histogram bin and reported with greater resolution than the bin resolution. For example, from a histogram with a bin resolution of 1 percent oxygen saturation units a centroid value is obtained with a resolution finer than 1 oxygen saturation unit, such as 74.3 percent oxygen saturation units. In some embodiments, the centroid calculation is adjusted to reduce the effects of noise and boundary conditions by setting a minimum threshold value above which the centroid calculation is performed and below which the centroid calculation is not performed, for example with a threshold fixed at a specified number of bin counts or at a ratio of the peak histogram count, for example 5 percent of the peak histogram count. Various numerical calculations of the centroid value are possible. Embodiments described herein are illustrative of the concept of the centroid measurement applied herein without limitation otherwise.

As has been described with a mixed-venous example with respect to FIG. 15, and herein for a central venous example with respect to FIG. 17, the central venous histogram is similarly illustrative of characteristics of a venous measurement site including herein (i.e., with the use of the centroid as an alternative to the peak) an oxygen saturation value coinciding with the centroid of the histogram that is consistent with values expected in from a venous blood-filled structure, in the range of 85 percent oxygen saturation or lower, or more typically in the range of 60 to 80 percent oxygen saturation, depending on the physiology and medical condition of an individual patient. A further characteristic of a venous histogram is a broadening of the histogram about either side of the centroid, for example, at half the maximum peak value, such that a lower boundary value and upper boundary value both exist, and wherein the oxygen saturation values enclosed by the lower and upper boundary values span values associated with venous blood-filled structures, and wherein the oxygen saturation values enclosed by the lower and upper boundaries may span a range of 5 to 20 oxygen saturation percent units. A further representative characteristic of a venous histogram is the absence of values associated with arterial oxygen saturation, that is of values above 85 percent oxygen saturation, or at and above 95 percent oxygen saturation, and depending on the physiology and medical condition of an individual patient.

In some embodiments, an oxygen saturation value associated with the centroid of the histogram is reported as the oxygen saturation measurement value obtained from the venous blood-filled structure, and the oxygen saturation values associated with the upper and lower FWHM (full with half maximum) boundaries reported as ancillary oxygen saturation values. In some embodiments, the difference between the upper and lower FWHM (full with half maximum) boundaries is reported as an ancillary oxygen saturation range as previously described. In some embodiments, other mathematical values representing the histogram or (where applicable) its upper and lower boundaries, or other characteristics, or computed minima, maxima, and standard deviation of such values are reported in similar manner. In further embodiments, mathematical functions are also used to model the distribution of values of the histogram, for example, the distribution of values are represented by a Gaussian function mathematical model or by a complementary error function mathematical model. In some embodiments, use of mathematical models provides enhancements to measurement accuracy by providing rigorous methods for the interpolation of values, and statistical methods to address measurement uncertainty.

In some embodiments, other sites and structures are measured. Examples shown are illustrative of the method, and do not limit the scope of the method. In still further embodiments, the concepts of peak value, centroid value, upper and lower boundary and histogram width as described above apply in equivalent manner to a graphical representation of a histogram obtained by the methods described, or to a numerical representation of a so-obtained histogram comprised of an array of values, or to any derived mathematical representation of the histogram which fundamentally describes a functional equivalent distribution of oxygen saturation values.

Figure 18:
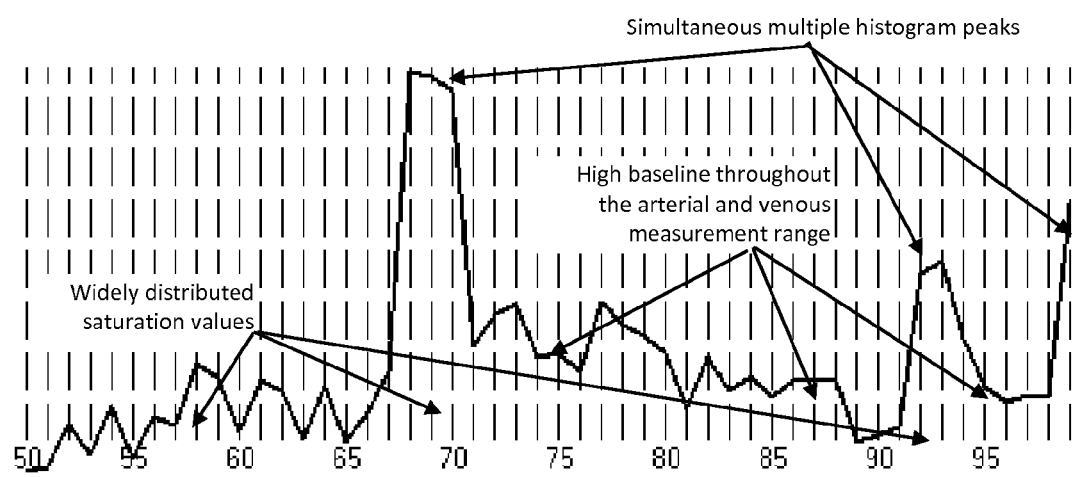
FIG. 18 illustrates a histogram of multi-modal oxygen saturation values with a probe not properly in position at a target organ.

In some embodiments, the method of using a histogram described herein allows the operator to determine if the probe is not optimally positioned and is likely to require corrections. FIG. 18 shows a histogram of oxygen saturation values obtained with the probe not in position at a desired target. This histogram is illustrative of characteristics of a mal-positioned measurement site including: widely distributed oxygen saturation values spanning the range of arterial and venous oxygen saturation measurements; simultaneous multiple histogram peaks; and a high baseline throughout the arterial and venous measurement range, or conversely expressed, a corresponding lack of ranges in which either venous or arterial baseline values are zero or near zero. These characteristics obtained individually or in combination inform the operator that the probe is not measuring either a venous or an arterial site with fidelity, and provide an effective noise baseline against which a signal is sought by positioning.

Probe Positioning

Figure 19:
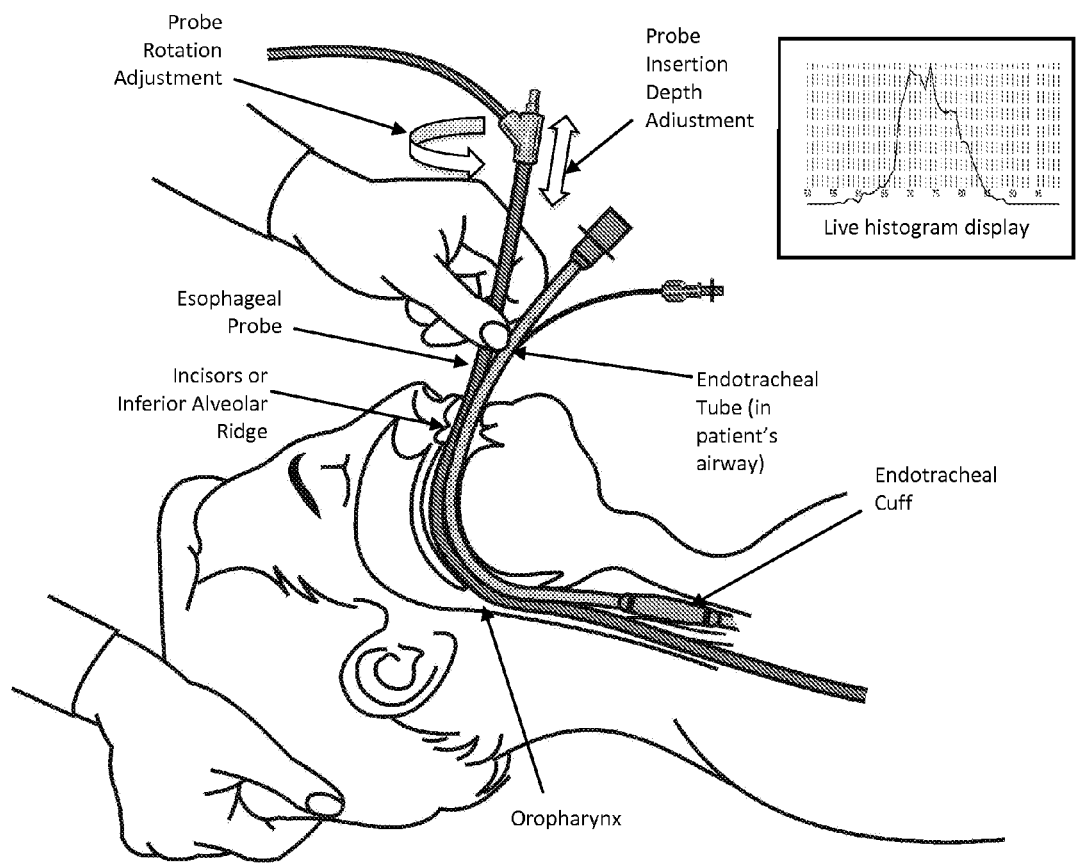
FIG. 19 illustrates operator positioning of a probe by using a displayed histogram.

FIG. 19 shows an operator positioning a probe as guided by the displayed histogram, by actions of insertion/retraction and rotation. In some embodiments, positioning of the probe can be executed with the following sequential steps, with the understanding that the sequence described is considered an exemplification of the principles of the present invention and is not intended to be limited to the embodiments described.

Initial oral introduction of a probe for the purpose of esophageal oximetric measurements by passage through the patient's oropharynx is in like manner to other esophageal medical devices comprised of flexible tubing such as an esophageal stethoscope or TEE, often in a patient who is anaesthetized, sedated, or otherwise unconscious, and wherein the patient's airway and breathing means has been previously established and protected by an endotracheal cuff or other means such as tracheotomy. In some embodiments, only the oximetric probe is inserted at one time as other devices simultaneously placed in the esophagus may interfere with sensor contact with the esophageal wall and the probe's effective operation. In other embodiments, a bias balloon, if used, is deflated during insertion and adjustment steps to facilitate both ease of insertion and adjustment and patient safety.

With reference to an esophageal deployment, a useful convention is to measure the longitudinal distance in centimeters (FIG. 7) to various cardiac structures i.e., from the patient's incisors or inferior alveolar ridge, and to measure a rotation angle in degrees from a reference defined to be an anterior facing direction from the esophagus (FIG. 8). From an established initial distance and known rotation it is possible to further navigate the probe. In some embodiments, the probe to be deployed has index markings which provide information on the probe's current depth and rotation. In preferred embodiments, the current technology provides interactive methods to adjust the probe's sensor from an approximate position to an optimally useful position. In some embodiments, initial approximate placement is made on the basis of general knowledge of esophageal and cardiac anatomy, for example, the left atrium is approximately 28 to 33 cm distant from the incisors in human adults. Alternatively, in some embodiments initial approximate placement of the probe is assisted by anatomical knowledge obtained by prior TEE placement, such as an observed distance from the incisors to a visualized cardiac structure such as the right atrium or left atrium. In other embodiments, initial placement of the probe is assisted by other signals such as an esophageal electrocardiogram, which is used to obtain biphasic P-waves in proximity to the left atrium. Proceeding from an initial placement approximately at the left atrium, which is an arterial blood-filled structure, and using a rotation of zero degrees (i.e., facing anterior from the esophagus), a method to subsequently locate a venous anatomical site in the vicinity of the right atrium involves the following steps:

As shown in FIGS. 7-10, known relative positions of cardiac structures in human adults are used to subsequently adjust from one anatomical site to the general location of another anatomical site, for example, the right atrium is approximately 5 cm distal to the left atrium, with a rotation of approximately 40 to 50 degrees to the right with respect to the anterior direction. Thus, to relocate the probe from a position at the left atrium to a position in general proximity to the right atrium will involve advancing the probe approximately 5 centimeters, and rotating the probe to the right. However, to account for individual anatomical variations that may present, small stepwise changes are made in the probe's depth and angular placement in order to incrementally assess the effects of the changes in position as per the displayed histogram.

When the initial target location is in proximity to the left atrium, an arterial blood filled structure, a histogram will be as shown in FIG. 16, with values consistent with an arterial oxygen saturation measurement in the range of 85 percent oxygen saturation or higher, or in a narrowly defined histogram in the range of 95 to 100 percent oxygen saturation, and simultaneously exhibiting an absence of values associated with venous oxygen saturation below 85 percent oxygen saturation.

For example, to locate a venous structure in the vicinity of the right atrium, the probe is gradually advanced more deeply into the esophagus, in short steps of approximately 1 to 2 cm in order that the histogram is interactively observed after each change in position. The immediate possible outcomes of a position change depend on the physiology of the measured site. In some embodiments, the associated histogram is a continuation of a pattern associated with an arterial oxygen saturation as in FIG. 16, or secondly, a with a histogram that becomes less arterial and more indeterminate as in FIG. 18 by exhibiting widely distributed values over both the arterial and venous measurement range, or thirdly, a histogram associated with a venous oxygen saturation values as in FIG. 17 wherein the peak of the histogram is consistent with values expected in from a venous blood-filled structure, in the range of 85 percent oxygen saturation or lower and including a lower boundary value and upper boundary value, and wherein the oxygen saturation values enclosed by the lower and upper boundaries are indicative of values associated with venous blood-filled structures, and an absence of values associated with arterial oxygen saturation, that is of values above 85 percent oxygen saturation.

In some embodiments, gradual changes in position spanning different physiological structures may cause gradual changes in histogram morphology, for example, as a new position reports less of an arterial associated histogram it may first report an increased baseline in an arterial histogram. In some embodiments, with a reported real time histogram, the operator is quickly be able to ascertain the effects of a change in position, and operator positioning becomes an interactive task assisted by the displayed histogram as in FIG. 19.

As shown in FIGS. 7 and 10, advancement of the probe approximately 5 cm from the initial location of the left atrium eventually bypasses the left atrium. To locate the venous blood-filled structure of the right atrium or inferior vena cava it is often necessary to rotate the probe to the right by some amount. Presuming a gradual rotation to approach the anatomical site, the initial location of a blood-filled venous structure is coincident with the gradual emergence of a histogram peak associated with venous values i.e., the venous peak in the histogram will begin to increase in amplitude. Subsequent adjustment of the probe to an optimal position at the venous structure is guided by a histogram in which a substantial increase in the venous peak with upper and lower boundaries is observed, and is coincident with a reduction in reported arterial values as described above. With the feedback mechanism of the histogram, the operator makes successive small adjustments to the probe in order to obtain a histogram which exhibits a maximal venous peak and minimal arterial reported values.

In some embodiments, once a structure to be measured has been optimally positioned using the methods described above, a bias balloon is inflated to expand the local diameter of the probe in the vicinity of the optical sensors, and thus to advance the optical sensor into closer proximity to the blood filled target venous structure by local thinning of the deformable esophageal tissue, and to stabilize the probe's position. For ongoing monitoring, the histogram continues to permit observation by the operator as to both reported parameters and the ongoing suitability of the measurement and position; for example, a diminishment of a venous histogram peak for a venous structure monitored continuously is an indication of the probe shifting out of optimal position. In some embodiments, the bias balloon is periodically deflated by manual or automated methods to allow the locally expanded esophageal tissue an interval for reperfusion, and is deflated for probe removal or adjustment to a new anatomical position.

The sequence above describes positioning of the probe from an arterial blood-filled structure to a venous blood filled structure using a histogram to reach the optimal position. In some embodiment, the approximate known relative positions of cardiac structures in human adults are used to preliminarily position the probe from one anatomical site to the approximate location of another anatomical site, and then with the feedback of the reported histogram the optimal location is obtained with gradual adjustments.

In some embodiments, a probe is configured to comprise a plurality of optical illumination sources and photo-detectors so that measurements are obtained from several anatomical sites simultaneously. In other embodiments, use of additional sensors comprises the use of additional oximetric measurement instrumentation or a suitable methods to multiplex multiple sensors. In one embodiment, two sensor sets are located with respect to one another at relative depths and rotations corresponding to the relative known cardiac positions of two blood filled structures, for example, the left atrium and right atrium, so that the oxygen saturation of blood in both structures is measured and monitored at the same time.

In another embodiment, multiple sets of sensors are located at predetermined angular orientations around the probe's central axis, for example, four sets of sensors are located at 90 degree rotational increments from each other, or six sets are located at 60 degree rotational increments from each other, or other increments, such that several histograms associated with several measurements are reported simultaneously and the optimal histogram, for example, corresponding with a desired venous measurement is selected from the family of available histograms without requiring further operator manipulation of the probe to achieve a successful measurement. In some embodiments, a probe with multiple sensors, and instrumentation reporting multiple histograms, is combined with automated software methods to select the histograms that are most representative of arterial and venous structures (i.e. using criteria described above), and to report the arterial and venous measurements so obtained.

Morphology of Signals Measured

In some embodiments, the time-varying morphology, or shape of the waveform of the photoplethysmographic data stream obtained from a sensor at a specific anatomical site, is used singly or in combination with an oxygen saturation histogram to provide further information on measurements obtained at a site and their underlying anatomy. In other embodiments, waveforms correlate with specific anatomical sites and functions coincident with the cardiac cycle.

Figure 23:
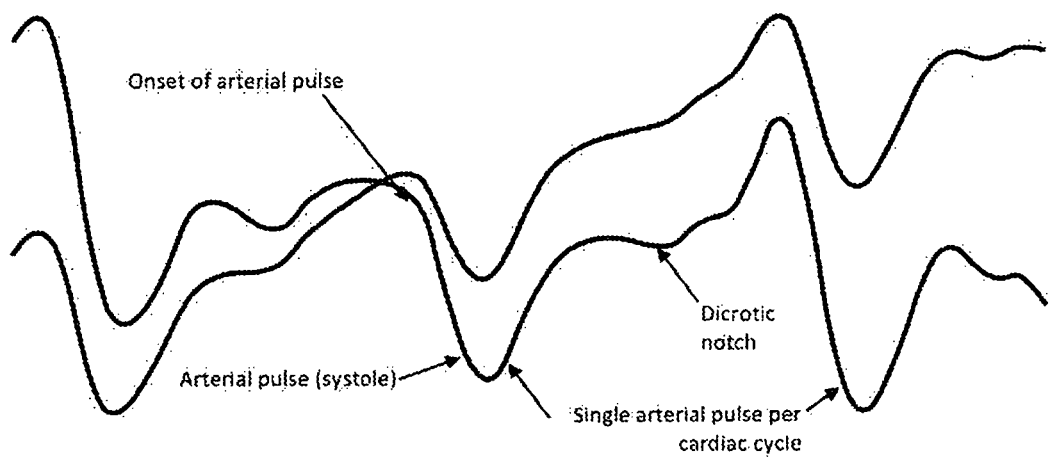
FIG. 23 illustrates peripheral pulse oximetry arterial waveform morphology.

Standard surface pulse oximetry of, for example, the extremity, the nose, the ear or other tissue, requires a pulsatile signal corresponding to arterial pulsation in the capillary bed of the measured tissue to perform a measurement. Pulse oximeter algorithms provide the measurement of arterial pulsation, and thus selectively accept arterial pulsations and reject, or otherwise compensate for, other signals or pulsations which are determined to be non-arterial in origin by means of established criteria. FIG. 23 shows the morphology of a time varying photoplethysmogram from a conventional pulse oximetry arterial waveform measured at a finger, wherein the occurrence of a measured arterial pulse is coincident with the increased optical absorbance of arterial blood perfusing the finger in the optical path of the sensor. Thus, the photoplethysmogram shows a decrease in measured signal intensity associated with the onset of the arterial pulse, and downward directed pulsation due to the increased optical absorbance of the arterial blood coincident with the arterial pulsation. Of note, by industry convention it is common for pulse oximeter monitors to display an inverted graphic representation of the plethysmographic absorbance waveform to show an upward-directed pulsation associated with the arterial pulse. Morphologic features of an arterial pulse include a single primary arterial pulse associated with systole during the cardiac cycle and, following this, a secondary smaller pulse feature representing the dicrotic notch which is associated with aortic valve closure.

Figure 21:
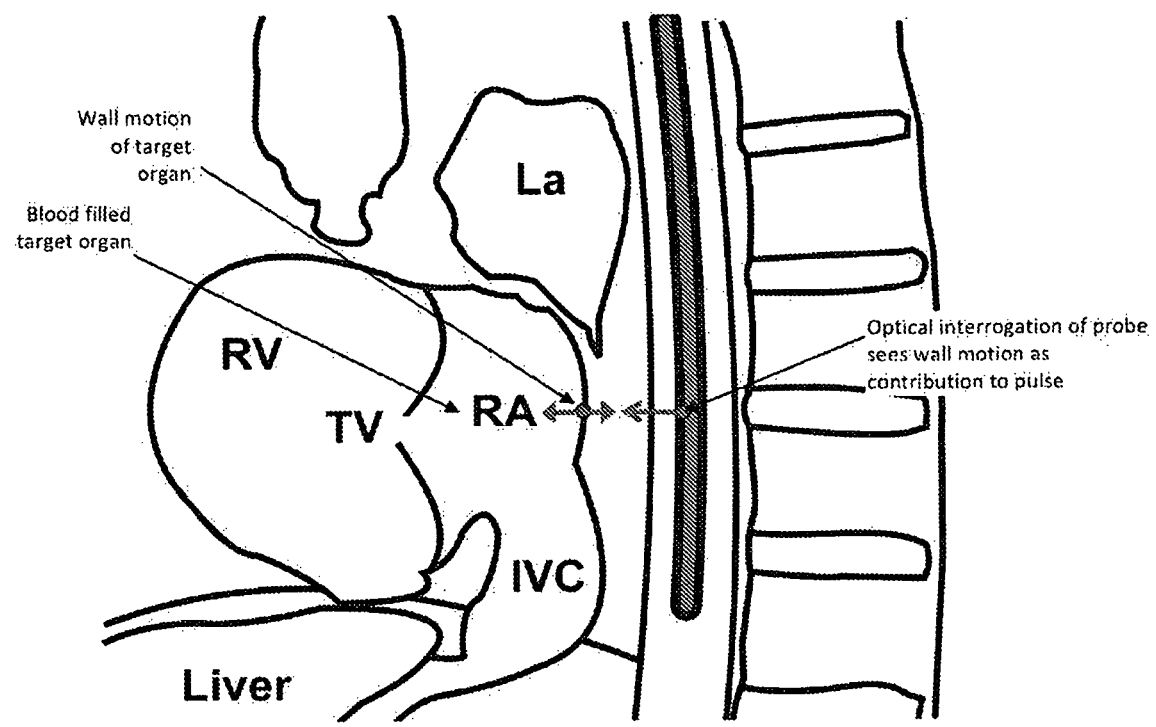
FIG. 21 illustrates wall motion of a blood containing structure.

In some embodiments, measurements and methods of the technology described herein include venous and arterial structures which, due to their anatomical origin and function, do not all exhibit morphology associated with arterial pulsation, and thus challenge conventional pulse oximeter techniques which selectively detect an arterial pulse. FIG. 21 illustrates the wall motion of blood containing structures. With reference to the figure, a target measurement site such as the right atrium comprises a blood containing structure, and pulsation or wall movement associated with the structure itself. Blood-filled structures such as cardiac chambers and major vessels are distinct measurement targets for pulse oximetric methods compared to arterially perfused capillary beds of, for example, the external finger, nose or ear. Wall motion of a blood filled structure contributes a time-varying optical signal to a sensor that is optically interrogating cardiac sites. Wall motion may generate an optical signal pulsation that is larger in magnitude than the pulse oximeter measurement at, for example, an extremity. When interrogated optically by conventional pulse oximetric methods, the finger, which is a common extremity site for oximeter sensors, transmits a small pulsation of arterial capillary origin in the presence of a relatively large signal comprising a stationary (i.e. non-pulsating) structure. Pulse amplitudes for conventional oximetric signals are in the range of 1 to 3% of the total signal in healthy perfused tissue, and as low as 0.1% in tissue that is poorly perfused.

Conversely, when using pulse oximetric methods for optical interrogation of a blood-filled structure, the optical signal returned from the blood-filled tissue comprises a much larger amount of blood than in conventional pulse oximetric targets. Further, the mechanism of pulsation in blood-filled structures, i.e., blood movements through the vessels or chambers coincident with shifts in the position of the vessel walls, differs from the capillary arterialization that is present in conventional pulse oximetry. The range of pulse amplitude as a percentage of the total signal in blood-filled structures may exceed 20% in particular vessels. Thus, optical signals with a large modulation arising from blood-filled structures are detected more easily than local capillary arterialization, which is present in the esophageal tissue surrounding the probe. Therefore, in some embodiments, it is possible to measure a larger venous signal originating distant from a smaller arterial one that the probe also senses. Structures such as the ones interrogated by the technology described herein are blood filled structures, in which volume and pressure changes occur in accordance with cardiac activity. In addition, flow patterns occur in a correlated manner, in relation to the above mentioned changes. Compositions, methods and systems described herein are configured to recognize changes in volume and flow in order to determine oxygen saturation values of the respective blood filled structures. For example, Table 1 shows the oxygen saturation and pulsation morphology which is associated with various anatomical sites:

TABLE 1

| | Arterial Oxygen Saturation Histogram | Venous Oxygen Saturation Histogram |
|---|---|---|
| Arterial Pulsation Waveform Morphology | Finger, other extremities | Pulmonary Artery |
| Venous Pulsation Waveform Morphology | Left Atrium | Right Atrium, Inferior Vena Cava, Superior Vena Cava |

Figure 22:
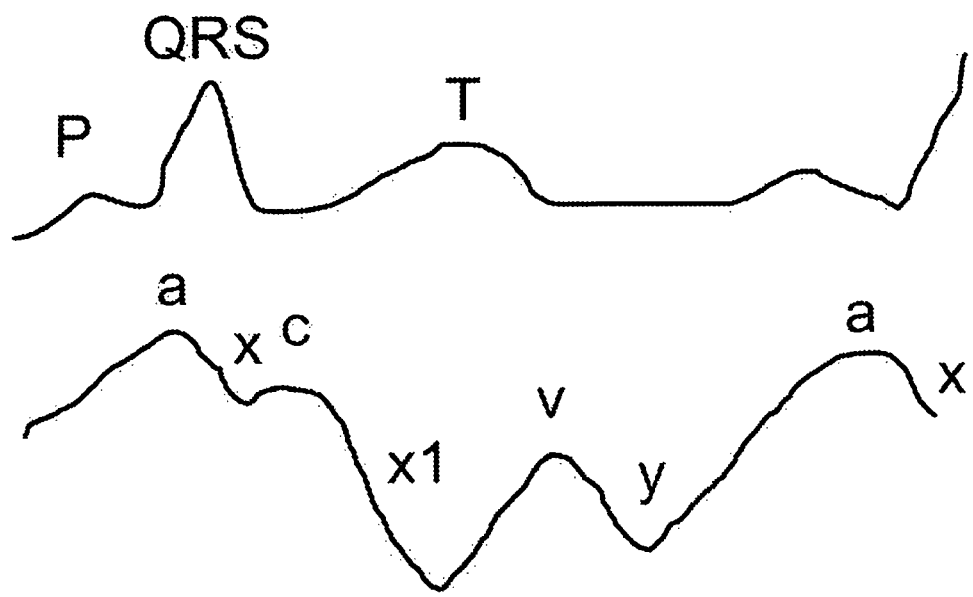
FIG. 22 illustrates a central venous pressure waveform adjacent to the cardiac cycle shown by an ECG waveform.

In some embodiments, the morphologies of the signals from blood filled structures provide methods to further optimize the measurement. FIG. 22 shows an exemplary central venous pressure waveform that is synchronized in time with an ECG waveform. Specific features of the morphology of a venous pressure waveform differ from an arterial waveform and are applicable in general to the morphology of waveforms obtained at other physiological sites with the methods described herein. Compared to the single primary pulsation associated with systole in an arterial waveform, the venous pressure waveform has at least two pulsatile peaks per cardiac cycle: a first peak (a) is associated with a rise in atrial pressure due to atrial contraction, and a second peak (v) is associated with a rise in atrial pressure as the atria refills during ventricular contraction. A third smaller peak (c) may or may not be evident from the protrusion of the tricuspid valve into the right atrium after valve closure. After the first peak of atrial contraction at (a), a pressure drop (x) associated with atrial relaxation may be observed. After the second peak of atrial filling occurs (v), a pressure drop (y) associated with atrial emptying may be observed. Thus the waveform morphology of a venous structure comprises two fundamental peaks (a,v) and an overall pattern of "axvy" is observed.

Figure 24:
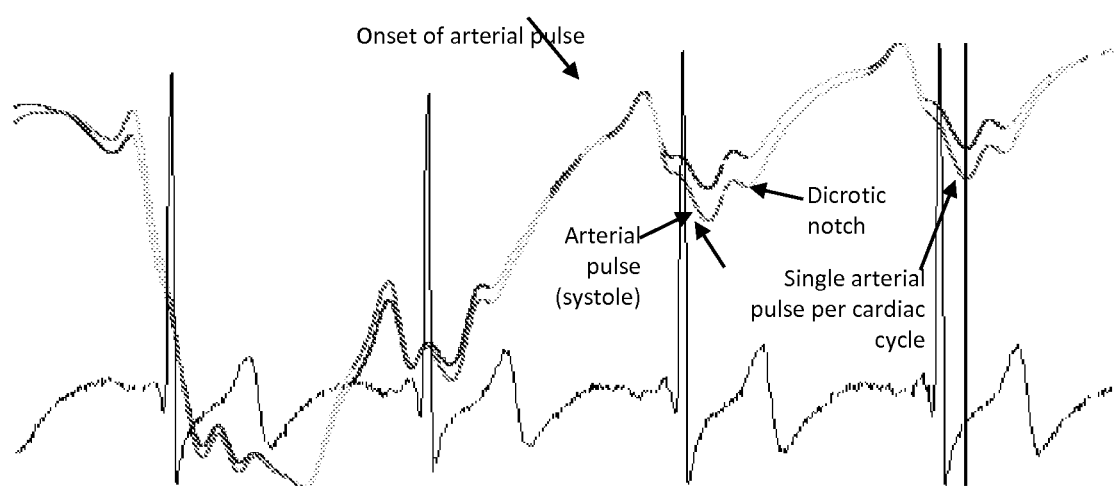
FIG. 24 illustrates a waveform morphology obtained at the right pulmonary artery as it crosses anterior to the esophagus.
Figure 25:
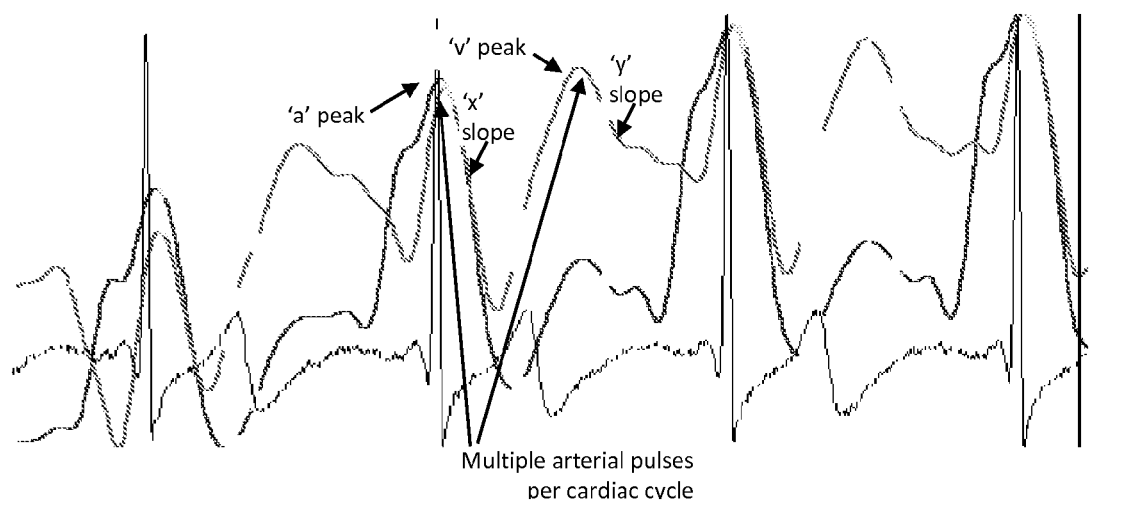
FIG. 25 illustrates a pulse waveform morphology obtained from the left atrium
Figure 26:
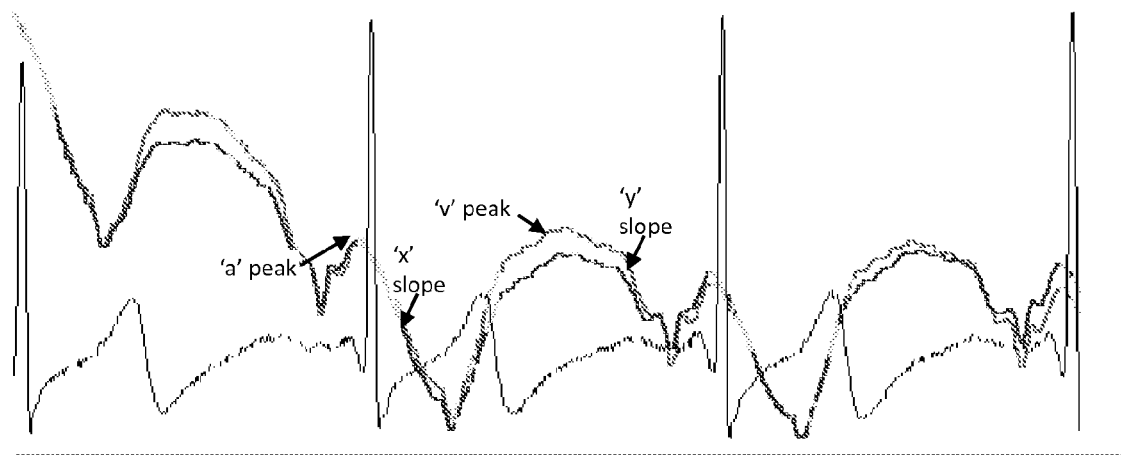
FIG. 26 illustrates a pulse waveform morphology obtained from the right atrium/inferior vena cava.

FIG. 24 shows waveform morphology obtained at the right pulmonary artery as it crosses anterior to the esophagus. As shown in Table 1, the pulmonary artery contains venous blood and a waveform morphology that is characteristically arterial, that is a single primary pulsation per cardiac cycle associated with systole, followed by a dicrotic notch. FIG. 25 shows the waveform morphology obtained at the left atrium. As shown in Table 1, the left atrium contains arterial blood and a waveform morphology that is characteristically venous. A first peak (a) is observed, and after this first peak a slope away from the peak (x); and a second peak (v), and after the second peak a slope away from the peak (y). The waveform morphology can therefore be observed to consist of two fundamental peaks (a, v) and an overall pattern of "axvy" is observed in each cardiac cycle. FIG. 26 shows the waveform morphology obtained at the right atrium/inferior vena cava. As shown in Table 1, the right atrium and inferior vena cava contain venous blood and a waveform morphology that is characteristically venous. A first peak (a) is observed and after this first peak a slope away from the peak (x); and a second peak (v) and after the second peak a slope away from the peak (y). The waveform morphology can therefore be observed to consist of two fundamental peaks (a,v) and an overall pattern of "axvy" is observed in each cardiac cycle.

Waveforms described above show that a pulsation characteristic of arterial signal morphology dominates the specific sites of the finger (FIG. 23, conventional arterial pulse oximetry at a body extremity) and pulmonary artery (FIG. 24, venous structure with arterial pulsation). A venous pulsation signal characteristic of the "axvy" morphology as shown in FIG. 22 is evident in the right atrium/inferior vena cava (FIG. 26, venous structure) and in the left atrium (FIG. 25, arterial structure with venous pulsation). The waveform measurement in FIG. 22 is derived from a central venous pressure measurement, and is therefore distinct from the optical measurements of blood filled structures wherein wall motion as described in FIG. 21 is a contributor to the optical signal detected by the sensor. Although pressure and wall motion do not yield equivalent signals, and the phase of the optical signal may be reversed from the pressure signal such that increases in one may correspond to decreases in the other, specific anatomical structures may manifest waveform morphologies consistent with venous as opposed to arterial pulsations.

In some embodiments, the venous or arterial morphology of the measured photoplethysmographic waveform is recognized in order to assist in the determination of the site per the table above. A correlation method or feature characterization is suitably employed to discriminate venous or arterial pulsation characteristics of the measurement site. These are aided by information provided from the patient's electrocardiogram, either surface or, for example, esophageal ECG electrodes, either of which would provide a method of identifying the cardiac cycle. Additionally, by knowing the cardiac cycle, selection of sub-regions of a waveform for selective processing is employed, wherein the sub-regions are potentially amenable to specific measurements, for example, the measurement of a venous structure is performed on a suitable signal pulsation at a time before or after systole, in order to minimize the pulsatile contributions of local arterial tissue.

All publications and patents mentioned in the above specification are herein incorporated by reference in their entirety for all purposes. Various modifications and variations of the described compositions, methods, and uses of the technology will be apparent to those skilled in the art without departing from the scope and spirit of the technology as described. Although the technology has been described in connection with specific exemplary embodiments, it should be understood that the technology as claimed should not be unduly limited to such specific embodiments. Indeed, various modifications of the described modes for carrying out the technology that are obvious to those skilled in pharmacology, biochemistry, medical science, or related fields are intended to be within the scope of the following claims.

EXPERIMENTAL EXAMPLES

Example 1

Post-Cardiac Surgery Patient in the Intensive Care Unit (ICU)

With Institutional Review Board approval, informed consent from the patient, and with USA Food and Drug Administration investigative device exemption (FDA/IDE) oversight of the test protocol, an esophageal probe with a longitudinally configured sensor optical surface portion with red and infrared light emitting diode (LED) illumination sources at 660 and 905 nanometers, and a silicon PIN photodiode (i.e., photodiode comprised of p-layer and n-layer of semiconductor with a wide intrinsic layer between the p- and n-layers which creates a wider depletion region within the device for improved quantum efficiency) with an active area of 7 $mm^2$ and an optical center distance of 1.75 cm to the center of the illumination source, was positioned in the esophagus of a 55 year old a male who had undergone surgery for mitral valve repair, and had been transferred to the intensive care unit (ICU) for post-operative recovery. With the probe positioned in the proximity of a target site, a bias balloon opposite the sensor optical surface was inflated with 3 cc of water to increase the local effective diameter of the probe, and to thin the esophageal wall. An ITEC oximeter module (Model M3-18, Protocol, A, ITEC Engineering, Pewaukee, Wis., USA) was used to alternately illuminate the red and infrared illumination sources in the probe and measure illumination at the detector. The raw photoplethysmographic data (i.e., red and infrared) from the ITEC module, which is a stream of the acquired values of the intensity of the signal received from the photodiode from each light source as modified by the light path through the tissue, was sent by serial data stream to a DELL Latitude D630 Notebook computer (Dell Computer Corporation, Austin, Tex., USA) with Windows XP PC, service pack 3 (Microsoft Corporation, Redmond Wash., USA), to store the data and to provide secondary operations on the data according the criteria described in FIG. 14 (flow chart) to thereby methods and systems for the measurement of venous and arterial oxygen saturation in the blood of blood-filled anatomical structures. generate a real time histogram representation of the data. A 10 second moving average of the histogram was used for displaying the histogram and positioning.

To record the oxygen saturation of blood in the right pulmonary artery as shown in FIG. 15, the probe was positioned at a depth of ~26 cm from the alveolar ridge, and the optical portion was rotated to be directed at the patient's anterior surface (i.e., 0 degrees by convention). By slowly advancing and rotating the probe, a histogram was obtained with maximal venous characteristics (see above) indicative of the right pulmonary target, which contains mixed venous blood. The morphology of the recorded and stored photoplethysmogram was arterial in morphology as per FIG. 24. Accordingly, a structure filled with blood having an oxygen saturation within a venous range, and an arterial photoplethysmogram waveform, is compatible with a right pulmonary artery source.

To record the oxygen saturation of blood in the left atrium as shown in FIG. 16, the probe was positioned at a depth of 28 cm and the optical portion was rotated to be directed at the patient's anterior surface (i.e., 0 degrees by convention). By slowly advancing and rotating the probe, a histogram was obtained with maximal arterial characteristics (see above) indicative of the left atrium, which contains arterial blood. The morphology of the recorded and stored photoplethysmogram was arterial in morphology as per FIG. 25. Accordingly, a structure filled with blood having an oxygen saturation within an arterial range, and an arterial photoplethysmogram waveform, is compatible with a left atrium source.

To record the oxygen saturation of blood in the right atrium/inferior vena cava, as shown in FIG. 17, the probe was positioned at a depth of ~33 cm from the alveolar ridge and the optical portion was rotated to be directed ~45 degree to the right from the patient's anterior surface. By slowly advancing and rotating the probe, a histogram was obtained with maximal venous characteristics (see above) indicative of the right atrium/inferior vena cava, which contains central venous blood. The morphology of the recorded and stored photoplethysmogram was venous in morphology as per FIG. 26. Accordingly, a structure filled with blood having an oxygen saturation within a venous range, and a venous photoplethysmogram waveform is compatible with a right atrium/inferior vena cava source.

To record the oxygen saturation of blood in an indeterminate location as shown in FIG. 18, the probe was positioned at a depth of ~28 cm from the alveolar ridge and the optical portion was rotated so that it was not directed at a blood-filled chamber. The resultant histogram in FIG. 18 shows 1.) multiple peaks and 2.) a high signal baseline (i.e., no zero values) spanning the venous to arterial oxygen saturation range, both of which characteristics are indicative of an indeterminate placement site which measures neither venous nor arterial structures.

Example 2

Adult Trauma Patient

A previously healthy farm worker is crushed by and pinned beneath a tractor, suffering internal injuries that include massive hemorrhage. His trachea is intubated in the field and he is transported to the nearest for acute care. On arrival, caregivers insert an esophageal probe. The probe is connected to the monitoring platform and all parameters are checked for functionality. The distal end of the probe is lubricated with water soluble gel. With the probe in the zero position equivalent to anterior in the anatomical sense, the probe is inserted into the oropharynx, advanced into the upper esophagus, and then assisted by pulling on the mandible in an anterior direction with the other hand. The initial depth of insertion is determined by a nomogram of average depth based on clinical and experimental data. With the probe at a given depth, and the rotation at zero, the p-max of the ECG electrodes is used to fine-tune the depth of insertion, by making small inward-outward adjustments, until the ECG signal is bi-phasic, and of maximum amplitude. This depth/rotational position is considered "home", and orients the pressure balloons in their native, designed positions. The probe's oxygen saturation module is thereby located approximately 5 cm more distal, and oriented ~45 degrees right (i.e., in relation to the patient in the supine position, i.e., looking toward the right chest), at or near the anatomic location of the right atrium (RA)/inferior vena cava (IVC) junction.

The oximetry software module, including histogram features, is used to acquire data, as described above. The operator identifies the preferred location for RA/IVC signals, begins data acquisition. If data from other locations is desired, the following movements are deployed for initial positioning, and then the above mentioned steps for fine-tuning per histogram are utilized:
1. RA/IVC—as above
2. Left atrium (LA)—turn the probe 45 degrees left (the oximetry module is now at 0 degrees, or anterior), and withdraw ~5 cm (the module is now posterior to the LA)
3. mixed venous (rPA)—from position 2 above, continue slow, progressive withdrawal (~2-5 cm), until the rPA histogram comes into view.

The initial data reveals normal LA oxygen saturation of 98-100% indicating that the lungs are functioning well, and completely saturating the blood flowing through the pulmonary vessels. The initial venous oxygen saturation values are near normal, with mixed and central venous oxygen saturation values of 70-75% and 75-80% respectively. The patient is resuscitated with crystalloid solution, and the intravascular space is filled. The depleted red cell mass results in a diminished delivery of oxygen to the peripheral tissues, combined with unchanged or increased total body oxygen consumption, and thus a falling central and mixed venous oxygen values, in the range of 50-60%. The patient is rushed to the operating room for emergent exploratory laparotomy and repair of vascular structures damaged during the tractor accident. The probe remains in place and is used as an intraoperative monitor.

After red blood cells become available, the patient is transfused, and the red cell mass is restored closer to normal. The venous oxygen saturation values returns to normal in a range of 70-75% as, more oxygen is carried to tissues, and extracted at the same rate, and the remaining oxygen content in venous blood that returns to the heart increases resulting in a rise in venous oxygen saturation. Resuscitation with crystalloid and red cells leads to intravascular overload, with the onset of pulmonary edema, compromising the lung's ability to adequately exchange oxygen. The heart becomes unable to handle the added filling volumes. Normal oxygen saturation values persist. Initially, pulmonary vascular congestion and pulmonary edema results in inadequate gas exchange, leading to a drop in systemic oxygen saturation values to 85-90% at first, followed by a decline in venous oxygen saturation values to the 65-70% range.

Based on this combination of values, the physician begins cardiac inotropic drugs to strengthen the heart's ability to pump, and to promote an increase in cardiac output, together with diuretic drugs to decrease intravascular volume, and an increase in inspired oxygen concentration. This combination of therapies results in a gradual return to normal oxygen saturation values. At the end of surgery, the patient is transported to the intensive care unit and remains sedated, with the trachea intubated, and mechanically ventilated, and with the esophageal probe in place to guide postoperative management of fluids, medications, and respiratory care.

Example 3

Pediatric Patient with Patent Foramen Ovale

A 1 year old child that has a connection between the right and the left atrium since birth with progressive shortness of breath and hypoxemia documented by low arterial oxygen saturations via surface pulse oximetry of the extremities. Radiologic and ultrasound studies demonstrate the presence of a patent foramen ovale (PFO). After induction of anesthesia, a probe is inserted into the esophagus and positioned. The initial data reveal a RA (central venous, right atrium) oxygen saturation in the normal range of 75-80%. The LA (left atrium systemic) oxygen saturation, however, indicates a lower than normal reading in the range of 85-90%, that varies with inspiratory effort, and with maneuvers that change intrathoracic pressures (e.g., the Valsalva maneuver). These data indicate shunting of blood across the defect from right to left, and thus pathologic mixing of venous and arterial blood primarily in the right and left atrium. Variation of values over time is attributed to a change in the degree of mixing that occurs during physiologic situations. The rPA value (mixed venous) oxygen saturation is also shows variability in the range of 65-85%. The surface, extremity oximeter shows a corresponding variability as venous blood shunts across to the systemic circulation through the PFO and is delivered to the peripheral arterial bed.

During the repair procedure, the interventional cardiologist places a closure device across the defect, and successfully closes the anatomic defect. The above described oxygen saturation values deviating from normal correct to their respective normal ranges within minutes. These data indicate that the procedure has been successfully performed. Additional maneuvers to attempt to change the degree of shunting, as performed prior to the procedure, no longer result in the changes before the repair. With all values in the normal range, the procedure is concluded.

Example 4

Geriatric Patient with Status Asthmaticus

A local rescue squad is called to a nursing home to respond to an elderly patient who is having difficulty breathing. Upon arrival, the patient is found in extreme respiratory distress, with rapid, shallow breathing, and cyanosis (blue skin color indicating hypoxia). The team intubates the trachea, and places an esophageal probe to establish baseline oxygen saturation values. Initial values, with the patient ventilated with 40% oxygen, shows a low LA reading of 70-75%, indicating inadequate gas exchange and oxygen saturation in the pulmonary circulation. Both central and mixed venous values are also decreased in the 40-50% range. Increased inspired oxygen at 100% shows only minimal benefit, with LA readings rising to the 80-85% range, and venous values rising minimally. Further therapy with administration of inhaled bronchodilator therapy gradually improves gas exchange in the lungs, and increases oxygen delivery to the pulmonary capillary bed. Oxygen saturation of pulmonary blood is improved, and LA oxygen saturation increases to 90-95%, with a coincident rise in venous values towards normal.

During transport of the patient to the hospital, the attending caregivers notice a sudden decrease in both LA and venous oxygen saturation readings, indicating a significant change in patient status. Examination of the patient reveals unequal breath sounds between the left and right sides of the chest that are attributed to a mal-positioning of the endotracheal tube into one of the mainstem bronchi. Adjustment results in equalization of breath sounds, resumption of adequate oxygen delivery to all lung fields, and improved gas exchange. LA oxygen saturation values return to the expected 90-95% range, and venous values also rise accordingly. The probe is left in place as the patient arrives in the emergency department, and its readings are used as caregivers make adjustments and further therapeutic interventions. It remains in place as the patient is transferred to the intensive care unit for definitive management.

We claim:

1. A method for measuring blood oxygen saturation in a blood-filled structure comprising:
   a) providing a system comprising:
      1) at least one oximeter sensor comprising;
         i) at least two light sources of differing wavelength;
         ii) at least one photodetector; and
         iii) a sensor housing comprising:
            a') a flexible tubular member;
            b') an optically transparent electrically isolated sheath; and
            c') a cable comprising at least one connector;
      2) a processor comprising:
         i) a controller adapted for analyzing a plurality of signals from said oximeter sensor, calculating oxygen saturation values from the signals, and generating a distribution of the relative frequency of occurrence of oxygen saturations obtained within defined intervals of oxygen saturation at a plurality of predetermined averaging intervals; and
      3) a display configured to output the distribution calculated by the processor;
   b) positioning said oximeter sensor in a position adjacent to a blood-filled structure of a subject while displaying said distribution and using said displayed information to optimize said positioning relative to said blood-filled structure; and
   c) measuring said blood oxygen saturation in said blood filled structure of said subject with said oximeter sensor at the optimized position.

2. The method of claim 1, wherein said subject is a mammal.

3. The method of claim 2, wherein said mammal is a human.

4. The method of claim 1, wherein said position is an esophageal position.

5. The method of claim 1, wherein said distribution permits determining whether said blood-filled structure is filled with venous blood, with arterial blood or with mixed venous and arterial blood.

6. The method of claim 1, wherein said blood-filled structure is the inferior vena cava, the right atrium, the pulmonary artery or the left atrium.

7. The method of claim 1, wherein the optical axis of said at least two light sources and said at least one detector are co-planar with the central axis of said tubular member.

8. The method of claim 1, wherein the optical center of said at least two light sources and the optical center of said at least one detector are at least 12 millimeters apart.

9. The method of claim 1, wherein said at least two light sources are light emitting diodes (LEDs) with wavelengths from 500 nanometers to 1100 nanometers.

10. The method of claim 1, wherein said at least two light sources are laser diodes with wavelengths from 500 nanometers to 1100 nanometers.

11. The method of claim 1, wherein the optical axis of said at least two light sources and said at least one detector are perpendicular to the central axis of said tubular member.

12. The method of claim 1, wherein the optical center of said at least two light sources and the optical center of said at least one detector are at least 4 millimeters apart.

13. The method of claim 1, wherein said sensor housing comprises a sheath, a sleeve comprising said at least two light sources, and said at least one detector.

14. The method of claim 1, wherein said flexible tubular member contains at least one internal lumen.

15. The method of claim 14, wherein said lumen is open at both ends of said tubular member.

16. The method of claim 15, wherein the diameter of said lumen is at least 3 millimeters.

17. The method of claim 1, wherein the torsion of said flexible tubular member is at least 150 gram(force)*cm per degree per cm length.

18. The method of claim 1, wherein said tubular member further comprises at least one pair of electrocardiogram electrodes on the outer surface.

19. The method of claim 18, wherein the positioning step further comprises using the electrocardiogram from said at least one pair of electrocardiogram electrodes to position said oximeter system adjacent to a predetermined blood-filled structure.

20. The method of claim 1, wherein said position is an airway position.

21. The method of claim 20, wherein said airway position is a tracheal position.

22. The method of claim 1, wherein said sensor housing further comprises an adjustable balloon configured to position said at least two light sources and said at least one detector adjacent to said blood-filled structure.

23. The method of claim 22, wherein said balloon is inflated by gas or by liquid.

24. The method of claim 22, further comprising measuring and displaying the internal wall pressure of said balloon.

25. The method of claim 22, wherein said balloon is inflated and deflated by manual or by automated operation.

26. The method of claim 1, wherein said system further comprises a stethoscope.

27. The method of claim 1, wherein said system further comprises at least one temperature sensor.

28. The method of claim 1, wherein said oximeter sensor includes a plurality of said light sources and photodetectors positioned to provide multiple simultaneous blood oxygen saturation measurements from multiple blood-filled structures.

29. The method of claim 1, wherein said display displays said distribution of said relative frequency of occurrence of oxygen saturations obtained within defined intervals
of oxygen saturation at a plurality of predetermined averaging intervals.

30. The method of claim 1, wherein the positioning step further comprises positioning said oximeter sensor with transesophageal echocardiography.

* * * * *